US008673352B2

(12) United States Patent
Sowden

(10) Patent No.: US 8,673,352 B2
(45) Date of Patent: Mar. 18, 2014

(54) MODIFIED RELEASE DOSAGE FORM

(75) Inventor: Harry S. Sowden, Glenside, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 1627 days.

(21) Appl. No.: 11/107,674

(22) Filed: Apr. 15, 2005

(65) Prior Publication Data
US 2006/0233881 A1 Oct. 19, 2006

(51) Int. Cl.
A61K 9/20 (2006.01)
(52) U.S. Cl.
CPC ................................ A61K 9/2022 (2013.01)
USPC ........................................................ 424/464
(58) Field of Classification Search
None
See application file for complete search history.

(56) References Cited

U.S. PATENT DOCUMENTS

| 582,438 | A | 5/1897 | Scheidler |
| 599,865 | A | 3/1898 | Richards |
| 2,307,371 | A | 1/1943 | Hileman |
| 2,996,431 | A | 8/1961 | Barry |
| 3,085,942 | A | 4/1963 | Magid et al. |
| 3,146,169 | A | 8/1964 | Spence et al. |
| 3,185,626 | A | 5/1965 | Baker |
| 3,279,995 | A | 10/1966 | Reid |
| 3,627,583 | A | 12/1971 | Troy et al. |
| 3,670,065 | A | 6/1972 | Eriksson et al. |
| 3,726,622 | A | 4/1973 | DeTroyer et al. |
| 3,760,804 | A | 9/1973 | Higuchi et al. |
| 3,804,570 | A | 4/1974 | Hoschele et al. |
| 3,832,252 | A | 8/1974 | Higuchi et al. |
| 3,851,638 | A | 12/1974 | Alexander |
| 4,076,819 | A | 2/1978 | Maffrand |
| 4,097,606 | A | 6/1978 | Chavkin et al. |
| 4,111,202 | A | 9/1978 | Theeuwes |
| 4,139,589 | A | 2/1979 | Beringer et al. |
| 4,139,627 | A | 2/1979 | Lane et al. |
| 4,173,626 | A | 11/1979 | Dempski et al. |
| 4,198,390 | A | 4/1980 | Rider |
| 4,218,433 | A | 8/1980 | Kooichi et al. |
| 4,230,693 | A | 10/1980 | Izzo et al. |
| 4,271,206 | A | 6/1981 | Fariel et al. |
| 4,273,793 | A | 6/1981 | Fariel et al. |
| 4,279,926 | A | 7/1981 | Bruzzese et al. |

(Continued)

FOREIGN PATENT DOCUMENTS

CN 1099262 A 3/1995
CN 1130867 A 9/1996

(Continued)

OTHER PUBLICATIONS

Leiberman, et al., *Pharmaceutical Dosage Forms—Tablets*, 1990, pp. 213-217, 327-329, vol. 2, $2^{nd}$ ed., Marcel Dekker, Inc.

(Continued)

*Primary Examiner* — Bethany Barham
(74) *Attorney, Agent, or Firm* — Laura A. Donnelly

(57) ABSTRACT

The present invention relates to a medicinal dosage form having a first core, a second core, and a shell that surrounds a first portion of each core and a fill material that covers a second portion of at least one core, wherein the fill material that is provided over at least one core is not in contact with any portion of the other core. e. The inventive dosage forms provide modified release of one or more active ingredients contained therein. The present invention also relates to methods for manufacturing such medicinal dosage forms.

10 Claims, 2 Drawing Sheets

(56) References Cited

U.S. PATENT DOCUMENTS

| | | |
|---|---|---|
| 4,292,017 A | 9/1981 | Doepel |
| 4,322,449 A | 3/1982 | Voss et al. |
| 4,362,757 A | 12/1982 | Chen et al. |
| 4,371,516 A | 2/1983 | Gregory et al. |
| 4,372,942 A | 2/1983 | Cimiluca |
| 4,392,493 A | 7/1983 | Niemeijer |
| 4,425,332 A | 1/1984 | James |
| 4,449,983 A | 5/1984 | Cortese et al. |
| 4,473,526 A | 9/1984 | Buhler et al. |
| RE31,764 E | 12/1984 | Voss et al. |
| 4,517,205 A | 5/1985 | Aldrich |
| 4,518,335 A | 5/1985 | Pujari |
| 4,533,345 A | 8/1985 | Louw |
| 4,543,370 A | 9/1985 | Porter et al. |
| 4,544,345 A | 10/1985 | Buhler et al. |
| 4,564,525 A | 1/1986 | Mitchell et al. |
| 4,569,650 A | 2/1986 | Kramer |
| 4,576,604 A * | 3/1986 | Guittard et al. ............... 424/473 |
| 4,610,884 A | 9/1986 | Lewis et al. |
| 4,643,894 A | 2/1987 | Porter et al. |
| 4,661,521 A | 4/1987 | Salpekar et al. |
| 4,663,147 A | 5/1987 | DePrince |
| 4,683,256 A | 7/1987 | Porter et al. |
| 4,686,212 A | 8/1987 | Ducatman et al. |
| 4,725,441 A | 2/1988 | Porter et al. |
| 4,749,575 A | 6/1988 | Rotman |
| 4,757,090 A | 7/1988 | Salpekar et al. |
| 4,762,719 A | 8/1988 | Forester |
| 4,781,714 A | 11/1988 | Eckenhoff et al. |
| 4,786,505 A | 11/1988 | Lovgren et al. |
| 4,801,461 A | 1/1989 | Hamel et al. |
| 4,802,924 A | 2/1989 | Woznicki et al. |
| 4,803,076 A | 2/1989 | Ranade |
| 4,813,818 A | 3/1989 | Sanzone |
| 4,816,262 A | 3/1989 | McMullen |
| 4,820,524 A | 4/1989 | Berta |
| 4,828,841 A | 5/1989 | Porter et al. |
| 4,851,226 A | 7/1989 | Julian et al. |
| 4,853,230 A | 8/1989 | Lovgren et al. |
| 4,857,330 A | 8/1989 | Stephens et al. |
| 4,863,742 A | 9/1989 | Panoz et al. |
| 4,865,849 A | 9/1989 | Conte et al. |
| 4,873,231 A | 10/1989 | Smith |
| 4,882,167 A | 11/1989 | Jang |
| 4,894,236 A | 1/1990 | Jang |
| 4,906,478 A | 3/1990 | Valentine et al. |
| 4,929,446 A | 5/1990 | Bartolucci |
| 4,965,027 A | 10/1990 | Takahashi |
| 4,978,483 A | 12/1990 | Redding, Jr. |
| 4,980,169 A | 12/1990 | Oppenheimer et al. |
| 4,980,170 A | 12/1990 | Schneider et al. |
| 4,983,394 A | 1/1991 | Hussein et al. |
| 4,984,240 A | 1/1991 | Keren-Zvi et al. |
| 4,999,226 A | 3/1991 | Schock et al. |
| 5,002,970 A | 3/1991 | Eby, III |
| 5,004,614 A | 4/1991 | Staniforth |
| 5,032,406 A | 7/1991 | Dansereau et al. |
| 5,059,112 A | 10/1991 | Wieser |
| 5,075,114 A | 12/1991 | Roche |
| 5,089,270 A | 2/1992 | Hampton |
| 5,133,892 A | 7/1992 | Chun et al. |
| 5,145,868 A | 9/1992 | von Sprecher et al. |
| 5,146,730 A | 9/1992 | Sadek et al. |
| 5,169,645 A | 12/1992 | Shukla et al. |
| 5,188,840 A | 2/1993 | Iida et al. |
| 5,200,191 A | 4/1993 | Steele et al. |
| 5,200,193 A | 4/1993 | Radebaugh et al. |
| 5,213,738 A | 5/1993 | Hampton et al. |
| 5,213,808 A | 5/1993 | Bar-Shalom et al. |
| 5,228,916 A | 7/1993 | Berta |
| 5,229,164 A | 7/1993 | Pins et al. |
| 5,232,706 A | 8/1993 | Palomo Coll |
| 5,275,822 A | 1/1994 | Valentine et al. |
| 5,286,497 A | 2/1994 | Hendrickson et al. |
| 5,368,863 A | 11/1994 | Eckenhoff et al. |
| 5,391,378 A | 2/1995 | Sanderson |
| 5,393,533 A | 2/1995 | Versic |
| 5,405,617 A | 4/1995 | Gowan, Jr. et al. |
| 5,405,642 A | 4/1995 | Gilis et al. |
| 5,407,686 A | 4/1995 | Patel et al. |
| 5,415,868 A | 5/1995 | Smith et al. |
| 5,424,075 A | 6/1995 | Daher et al. |
| 5,427,614 A | 6/1995 | Wittwer et al. |
| 5,433,951 A | 7/1995 | Serajuddin et al. |
| 5,436,026 A | 7/1995 | Berta |
| 5,456,920 A | 10/1995 | Matoba et al. |
| 5,459,983 A | 10/1995 | Sadek et al. |
| 5,462,747 A | 10/1995 | Radebaugh et al. |
| 5,464,631 A | 11/1995 | Hoover et al. |
| 5,464,633 A | 11/1995 | Conte et al. |
| 5,489,436 A | 2/1996 | Hoy et al. |
| 5,510,385 A | 4/1996 | Stroppolo et al. |
| 5,511,361 A | 4/1996 | Sauter |
| 5,538,125 A | 7/1996 | Berta |
| 5,558,879 A | 9/1996 | Chen |
| 5,559,110 A | 9/1996 | Aungst |
| 5,578,336 A | 11/1996 | Monte |
| 5,593,696 A | 1/1997 | McNally et al. |
| 5,609,010 A | 3/1997 | Sauter |
| 5,610,214 A | 3/1997 | Olson |
| 5,614,207 A | 3/1997 | Shah et al. |
| 5,626,875 A | 5/1997 | Ballester Rodes et al. |
| 5,627,971 A | 5/1997 | Miernik |
| 5,630,871 A | 5/1997 | Jordan |
| 5,641,536 A | 6/1997 | Lech et al. |
| 5,654,005 A | 8/1997 | Chen et al. |
| 5,658,589 A | 8/1997 | Parekh et al. |
| 5,679,406 A | 10/1997 | Berta |
| 5,681,584 A | 10/1997 | Savastano et al. |
| 5,683,719 A | 11/1997 | Newton |
| 5,711,961 A | 1/1998 | Reiner et al. |
| 5,738,874 A | 4/1998 | Conte et al. |
| 5,753,265 A | 5/1998 | Bergstrand et al. |
| 5,795,588 A | 8/1998 | Sauter |
| 5,807,579 A | 9/1998 | Vilkov et al. |
| 5,807,580 A | 9/1998 | Luber |
| 5,817,338 A | 10/1998 | Bergstrand et al. |
| 5,824,338 A | 10/1998 | Jacobs et al. |
| 5,827,535 A | 10/1998 | Stone |
| 5,827,874 A | 10/1998 | Meyer et al. |
| 5,830,501 A | 11/1998 | Dong et al. |
| 5,830,502 A | 11/1998 | Dong et al. |
| 5,834,035 A | 11/1998 | Osada et al. |
| 5,837,301 A | 11/1998 | Arnott et al. |
| 5,849,327 A | 12/1998 | Berliner et al. |
| 5,853,760 A | 12/1998 | Cremer |
| 5,861,173 A | 1/1999 | Nishioka et al. |
| 5,871,781 A | 2/1999 | Myers et al. |
| 5,912,013 A | 6/1999 | Rudnic et al. |
| 5,942,034 A | 8/1999 | Brehant et al. |
| 5,980,944 A | 11/1999 | Stevens et al. |
| 5,997,903 A | 12/1999 | Dietrich et al. |
| 5,997,905 A | 12/1999 | McTeigue et al. |
| 6,001,391 A | 12/1999 | Zeidler et al. |
| 6,013,281 A | 1/2000 | Lundberg et al. |
| 6,022,554 A | 2/2000 | Lee et al. |
| 6,077,541 A | 6/2000 | Chen et al. |
| 6,090,401 A | 7/2000 | Gowan et al. |
| 6,096,340 A | 8/2000 | Chen et al. |
| 6,103,257 A | 8/2000 | Nisonoff |
| 6,103,260 A | 8/2000 | Luber et al. |
| 6,110,499 A | 8/2000 | Shivanand et al. |
| 6,110,500 A | 8/2000 | Kim |
| 6,117,479 A | 9/2000 | Hogan et al. |
| 6,120,802 A | 9/2000 | Breitenbach et al. |
| 6,123,861 A | 9/2000 | Santini et al. |
| 6,149,939 A | 11/2000 | Strumor et al. |
| 6,149,943 A | 11/2000 | McTeigue et al. |
| 6,159,499 A | 12/2000 | Seth |
| 6,174,548 B1 | 1/2001 | Chen et al. |
| 6,183,776 B1 | 2/2001 | Depui et al. |
| 6,200,590 B1 | 3/2001 | Eley |
| 6,207,198 B1 | 3/2001 | Seth |
| 6,217,902 B1 | 4/2001 | Tanner et al. |

(56) References Cited

U.S. PATENT DOCUMENTS

| | | |
|---|---|---|
| 6,224,910 B1 | 5/2001 | Ullah et al. |
| 6,248,355 B1 | 6/2001 | Seth |
| 6,248,361 B1 | 6/2001 | Johnson et al. |
| 6,248,760 B1 | 6/2001 | Wilhelmsen |
| 6,264,985 B1 | 7/2001 | Cremer |
| 6,270,805 B1 | 8/2001 | Chen et al. |
| 6,274,162 B1 | 8/2001 | Steffenino et al. |
| 6,294,200 B1 | 9/2001 | Conte et al. |
| 6,322,819 B1 | 11/2001 | Burnside et al. |
| 6,331,316 B1 | 12/2001 | Ullah et al. |
| 6,350,398 B1 | 2/2002 | Breitenbach et al. |
| 6,365,185 B1 | 4/2002 | Ritschel et al. |
| 6,372,252 B1 | 4/2002 | Blume et al. |
| 6,375,963 B1 | 4/2002 | Repka et al. |
| 6,394,094 B1 | 5/2002 | McKenna et al. |
| 6,428,810 B1 | 8/2002 | Bergstrand et al. |
| 6,489,346 B1 | 12/2002 | Phillips |
| 6,555,139 B2 | 4/2003 | Sharma |
| 6,569,457 B2 | 5/2003 | Ullah et al. |
| 6,602,522 B1 | 8/2003 | Chen et al. |
| 6,613,354 B2 | 9/2003 | Depui et al. |
| 6,726,927 B2 | 4/2004 | Chen |
| 6,727,213 B2 | 4/2004 | Waschenbach et al. |
| 6,730,646 B1 | 5/2004 | Waschenbach et al. |
| 6,742,646 B2 | 6/2004 | Sowden et al. |
| 6,767,200 B2 | 7/2004 | Sowden et al. |
| 6,837,696 B2 | 1/2005 | Sowden et al. |
| 6,913,766 B1 | 7/2005 | Krumme et al. |
| 6,982,094 B2 | 1/2006 | Sowden |
| 7,122,143 B2 | 10/2006 | Sowden et al. |
| 7,387,793 B2 * | 6/2008 | Venkatesh et al. ............ 424/489 |
| 7,416,738 B2 * | 8/2008 | Sowden et al. ............... 424/471 |
| 2001/0001280 A1 | 5/2001 | Dong et al. |
| 2002/0028240 A1 | 3/2002 | Sawada et al. |
| 2002/0051807 A1 | 5/2002 | Faour et al. |
| 2002/0082299 A1 | 6/2002 | Meyer |
| 2003/0059466 A1 | 3/2003 | Seth |
| 2003/0060393 A1 | 3/2003 | Waschenbach et al. |
| 2003/0066068 A1 | 4/2003 | Gutta et al. |
| 2003/0068367 A1 | 4/2003 | Sowden et al. |
| 2003/0068373 A1 | 4/2003 | Luber et al. |
| 2003/0070903 A1 | 4/2003 | Sowden |
| 2003/0072799 A1 | 4/2003 | Sowden et al. |
| 2003/0086973 A1 | 5/2003 | Sowden et al. |
| 2003/0124183 A1 | 7/2003 | Sowden |
| 2003/0190362 A1 | 10/2003 | Sackler et al. |
| 2003/0232082 A1 | 12/2003 | Li et al. |
| 2003/0235616 A1 | 12/2003 | Sowden et al. |
| 2005/0074514 A1 | 4/2005 | Anderson |

FOREIGN PATENT DOCUMENTS

| | | |
|---|---|---|
| CN | 1183047 A | 5/1998 |
| DE | 2710307 | 9/1977 |
| DE | 3629994 A1 | 3/1988 |
| DE | 19834180 A1 | 2/2000 |
| DE | 19925710 A | 12/2000 |
| DE | 19954420 A1 | 5/2001 |
| DE | 19963569 A1 | 7/2001 |
| EP | 88556 B1 | 9/1983 |
| EP | 60023 B1 | 8/1984 |
| EP | 237200 B1 | 2/1987 |
| EP | 788790 A2 | 8/1987 |
| EP | 239983 B1 | 10/1987 |
| EP | 325492 A1 | 7/1989 |
| EP | 387885 B1 | 9/1990 |
| EP | 455599 A1 | 11/1991 |
| EP | 294993 B1 | 12/1991 |
| EP | 861659 A1 | 2/1992 |
| EP | 481547 A1 | 4/1992 |
| EP | 531524 B1 | 3/1993 |
| EP | 247983 B1 | 7/1993 |
| EP | 572731 A1 | 12/1993 |
| EP | 646650 A2 | 4/1995 |
| EP | 496437 B1 | 7/1996 |
| EP | 740938 | 11/1996 |
| EP | 864324 B1 | 3/1997 |
| EP | 519144 B1 | 8/1997 |
| EP | 619854 B1 | 3/1998 |
| EP | 834516 B1 | 4/1998 |
| EP | 861659 A | 9/1998 |
| EP | 950402 B1 | 2/1999 |
| EP | 1029892 B1 | 8/2000 |
| EP | 1077065 A1 | 2/2001 |
| EP | 1138661 A1 | 10/2001 |
| FR | 2011960 | 3/1970 |
| FR | 2604904 A1 | 4/1998 |
| GB | 866681 | 4/1961 |
| GB | 994742 | 5/1961 |
| GB | 888038 | 1/1962 |
| GB | 936386 | 9/1963 |
| GB | 1144915 | 3/1969 |
| GB | 1372040 | 12/1971 |
| GB | 1372040 A | 10/1974 |
| GB | 1464388 | 2/1977 |
| GB | 1510772 | 5/1978 |
| GB | 759081 | 10/1986 |
| GB | 2197778 A | 6/1988 |
| GB | 2284760 A | 6/1995 |
| JP | 63-10719 | 1/1988 |
| JP | Sho B1 125691 | 5/1988 |
| JP | Hei 3 232815 | 10/1991 |
| JP | Hei 5 345721 | 12/1993 |
| JP | 7-242535 | 9/1995 |
| NL | 8602556 | 5/1988 |
| WO | WO 89/11968 | 12/1989 |
| WO | WO 92/22284 A | 12/1992 |
| WO | WO 94/06416 A1 | 3/1994 |
| WO | WO 94/07470 A1 | 4/1994 |
| WO | WO 95/02396 A1 | 1/1995 |
| WO | WO 95/15156 | 6/1995 |
| WO | WO 97/06695 A1 | 2/1997 |
| WO | WO 97/15293 A2 | 5/1997 |
| WO | WO 97/49384 | 12/1997 |
| WO | WO 98/20870 A1 | 5/1998 |
| WO | WO 99/02136 A1 | 1/1999 |
| WO | WO 99/06157 | 2/1999 |
| WO | WO 99/32092 A1 | 7/1999 |
| WO | WO 99/51209 A1 | 10/1999 |
| WO | WO 99/56730 A1 | 11/1999 |
| WO | WO 99/62496 A | 12/1999 |
| WO | WO 99/62496 A1 | 12/1999 |
| WO | WO 00/18447 A2 | 4/2000 |
| WO | WO 00/25755 A1 | 5/2000 |
| WO | WO 01/28558 | 4/2001 |
| WO | WO 01/49815 A2 | 7/2001 |
| WO | WO 01/58433 | 8/2001 |
| WO | WO 01/85437 A1 | 11/2001 |
| WO | WO 02/11702 A2 | 2/2002 |
| WO | WO 02/19833 A2 | 3/2002 |
| WO | WO 03/007917 A1 | 1/2003 |
| WO | WO 03/026626 A | 4/2003 |
| WO | WO 03/028620 A | 4/2003 |
| WO | WO 03/063840 A2 | 8/2003 |
| WO | WO 03/080026 A | 10/2003 |
| WO | WO 2004/010978 A | 2/2004 |
| WO | WO 2004/066982 A | 8/2004 |
| WO | WO 2004/112756 A | 12/2004 |
| WO | WO 2006/047493 A | 5/2006 |

OTHER PUBLICATIONS

Elizabeth Carbide Die Co., Inc., *The Elizabeth Companies Tablet Design Training Manual*, p. 7, McKeesport, PA.

Lachman, et al., *The Theory and Practice of Industrial Pharmacy*, 1986. Chapter 11, 3rd ed.

International Search Report dated Feb. 26, 2003 for PCT/US02/31022.

International Search Report dated Mar. 3, 2003 for PCT/US02/31117.

International Search Report dated Feb. 20, 2003 for PCT/US02/31115.

(56) References Cited

OTHER PUBLICATIONS

International Search Report dated Feb. 20, 2003 for PCT/US02/31164.
International Search Report dated Jan. 8, 2004 for PCT/US03/08891.
International Search Report dated Feb. 11, 2003 for PCT/US02/31024.
International Search Report dated Feb. 6, 2003 for PCT/US02/31163.
European Search Report EP05253780 dated Aug. 2006.
Catellani et al. Internation Journal of Pharmaceutics vol. 88(1992) 285-291 "Centrifugal die filling system in a new rotary tablet machine."
Ceschel, G.C., et al., "Sugar Coating of Tablets", Bollettino Chimico Farmaceutico, 1980, pp. 127-134, vol. 119, Milan Italy.
Cobby, John et al., "Influence of Shape Factors on Kinetics of Drug Release from Matrix Tablets I: Theoretical". Journal of Pharmaceutical Sciences, May 1974, vol. 63, No. 5, pp. 725-732.
Cobby, John et al., "Influence of Shape Factors on Kinetics of Drug Release from Matrix Tablets II: Experimental". Journal of Pharmaceutical Sciences, May 1974, vol. 63, No. 5, pp. 732-737.
Cleave, J.P., "Some geometrical considerations concerning the design of tables". J. Pharm. Pharmacol, 1965, pp. 698-702.
Cuff & Rauf Pharm Tech Jun. 1998 96-106 "A Preliminary Evaluation of Injection Molding as a Technology to Produce Tablets."
Edwards, W.P.P., "Pan Coating". The Science of Sugar Confectionery, 2000, pp. 95-100, 1st Edition, The Royal Society of Chemistry, London, England.
Desai, S.J. et al., "Investigation of Factors Influencing Release of Solid Drug Dispersed in Inert Matrices". Journal of Pharmaceutical Sciences, Oct. 1965, vol. 54, No. 10, pp. 1459-1464.
"Electrostatics in Continuous Tablet Coating", Manufacturing Chemist, Oct. 1998, vol. 69, No. 10. pp. 13-16.
Eith, L., et al., "Injection-Moulded Drug-Delivery Systems", Manufacturing Chemist (Jan. 1987), pp. 21-25.
Fegely, Kurt A., et al. The Effect of Tablet Shape on the Perception of High Gloss Film Coating System, Opaglos 2, High Gloss Film Coating System, COLORCON, Mar. 18, 2002.
Gunsel, Willian., C. et al. "Compression-Coated and Layer Tablets", Pharmaceutical Dosage Forms-Tablets, 1989, pp. 247-284. 2nd Edtion, vol. 1, Marcel Dekker, Inc. New York.
Hansson, Arne G., et al., "Perforated Coated Tablets for Controlled Release of Durgs at a Constant Rate", Journal of Pharmaceutical Sciences, Apr. 1988, vol. 77, No. 4, pp. 322-324.
Higuchi, T., "Mechanism of Sustained-Action Medication—Theoretical Analysis of Rate of Release of Solid Drugs Dispersed in Solid Matriced". Journal of Pharmaceutical Sciences, Dec. 1963, vol. 52, No. 12, pp. 1145-1149.
Higuchi, Takeru, "Rate of Release of Medicaments from Ointment Bases Containing Drugs in Suspension". Journal of Pharmaceutical Sciences, Oct. 1961, vol. 50, pp. 874-875.
Hsieh, Dean S.T. et al., "Zero-Order Controlled-Release Polymer Matricas for Micro and Macromolecules". Journal of Pharmaceutical Sciences, Jan. 1983, vol. 72, No. 1, pp. 17-22.
Itoh. International Journal of Pharmaceutics 238 (2002) 153-160.
Kim, Chemg-ju, "Compressed Donut-Shaped Tablets with Zero-Order Release Kinetics", Pharmaceutical Research, Jul. 1994, vol. 12, No. 7, pp. 1045-1048.
Lipper, R.A. et al., "Analysis of Theoretical Behavior of a Proposed Zero-Order Drug Delivery System". Journal of Pharmaceutical Sciences, Feb. 1977, vol. 66, No. 2, pp. 163-164.
Maffione, G., et al., "High-Viscosity HPMC as a Film-Coating Agent", Drug Development and Industrial Pharmacy, 1993, pp. 2043-2053, vol. 19, No. 16, Marcel Dekker, Inc. New York.
Minifie, Bernard C., Chocolate, Cocoa and Confectionary: Science and Technology, Jan. 1980, pp. 608-613, 2nd Edition, AVI Publishing Company, Inc., Westport, CT.
Nelson, K.G. et al., "Constant-Release Diffusion Systems—Rate Control by Means of Geometric Configuration". American Chemical Society, 1987, Chap. 24, pp. 325-340.
Porter, Stuart C., PhD., "Tablet Coating—Part 1", Drug Cosmet, Ind., May 1981, pp. 46-53 and 86-93, vol. 128.
Remington The Science and Practice of Pharmacy, pp. 208-209 (2000).
Rosato, Dominick V. et al., Injection Molding Handbook, 1986, Van Nostrand Reinhold Company.
Sangalli, M.E. et al., "Inert Monolithic Device with Central Hole for Constant Drug Release". Proceed Intern: Symp. Control. Rel Biosct. Meter. 20(1993), Controlled Release Society, Inc. pp. 316-317.
Samuelov, Y., et al., "Sustained Release of Drugs from Ethylcellulose-Polyethyiene Glycol Films and Kinetics of Drug Release". Journal of Pharmaceutical Sciences, Mar. 1979. vol. 68, No. 3, pp. 325-329.
Schneider, H., et al., "Contribution to Sugar Coating Tablets". Pharmaceutica Acta Helvetiae, pp. 394-410, vol. 43.
USP 24, 2000 Version, 19-20 and 856 (1999).
Vehicle. Http://www2.merriam-webster.com/cgi-bin/mwmednim. Accessed Apr. 18, 2009.

\* cited by examiner

MODIFIED RELEASE DOSAGE FORM

FIELD OF THE INVENTION

This invention relates to dosage forms providing modified release of one or more active ingredients contained therein.

BACKGROUND OF THE INVENTION

Modified release pharmaceutical dosage forms have long been used to optimize drug delivery and enhance patient compliance, especially by reducing the number of doses of medicine the patient must take in a day. In some instances, it is also desirable for a dosage form to deliver more than one drug at different rates or times. Modified release dosage forms should ideally be adaptable so that release rates and profiles can be matched to physiological and chronotherapeutic requirements. Because the onset and duration of the therapeutic efficacy of drugs vary widely, as do their absorption, distribution, metabolism, and elimination, it is often desirable to modify the release of different drugs in different ways, or to have a first dose of drug (active ingredient) immediately released from the dosage form, while a second dose of the same or a different drug is released in a modified, e.g. delayed, pulsatile, repeat action, controlled, sustained, prolonged, extended, or retarded manner.

Well-known mechanisms by which a dosage form (or drug delivery system) can deliver drug at a controlled rate (e.g. sustained, prolonged, extended or retarded release) include diffusion, erosion, and osmosis. It is often practical to design dosage forms that use a combination of the above mechanisms to achieve a particularly desirable release profile for a particular active ingredient.

An important objective of modified release dosage forms is to provide a desired blood concentration versus time (pharmacokinetic, or PK) profile for the drug. Fundamentally, the PK profile for a drug is governed by the rate of absorption of the drug into the blood, and the rate of elimination of the drug from the blood. To be absorbed into the blood (circulatory system), the drug must first be dissolved in the gastrointestinal fluids. For those relatively rapidly absorbed drugs whose dissolution in gastrointestinal fluids is the rate-limiting step in drug absorption, controlling the rate of dissolution (i.e. drug release from the dosage form) allows the formulator to control the rate of drug absorption into the circulatory system of a patient. The type of PK profile, and correspondingly, the type of dissolution or release profile desired, depends on, among other factors, the particular active ingredient and physiological condition being treated.

One particularly desirable PK profile is achieved by a dosage form that delivers a delayed release dissolution profile, in which the release of one or more doses of drug from the dosage form is delayed for a pre-determined time after contacting of the dosage form by a liquid medium, such as for example, after ingestion by the patient. The delay period ("lag time") can be followed either by prompt release of the active ingredient ("delayed burst"), or by sustained (prolonged, extended, or retarded) release of the active ingredient ("delayed then sustained"). U.S. Pat. No. 5,464,633, for example, discloses delayed-release dosage forms in which an external coating layer was applied by a compression coating process. The coating level ranged from 105 percent to 140 percent of the weight of the core in order to yield product with the desired time delayed profile.

One particularly desirable type of delayed release PK profile is obtained from a "pulsatile" release profile, in which for example, a first dose of a first drug is delivered, followed by a delay period ("lag time") during which there is substantially no release of the first drug from the dosage form, followed by either prompt or sustained release of a subsequent dose of the same drug. In one particularly desirable type of pulsatile drug delivery system, the first dose is released essentially immediately upon contacting of the dosage form with a liquid medium. In another particularly desirable type of pulsatile drug delivery system, the delay period corresponds approximately to the time during which a therapeutic concentration of the first dose is maintained in the blood. Pulsatile delivery systems are particularly useful for applications where a continuous release of drug is not ideal. Examples of this are drugs exhibiting first pass metabolism by the liver, drugs that induce biological tolerance, i.e. the therapeutic effect decreases with continuous presence of the drug at the site of action, and drugs whose efficacy is influenced by circadian rhythms of body functions or diseases. One typical pulsatile dosage form design contains the first dose of drug in an exterior coating, or shell, while subsequent doses of drug are contained in underlying layers of subcoatings, or a central core. PCT Publication No. WO99/62496, for example, discloses a dosage form comprising an immediate-release dose of drug contained within an overcoat applied onto the surface of the semi-permeable membrane of an osmotic dosage form. U.S. Pat. Nos. 4,857,330 and 4,801,461, disclose dosage forms comprising an exterior drug coat that surrounds a semi-permeable wall, which in turn surrounds an internal compartment containing a second dose of drug, and comprises exit means for connecting the interior of the dosage form with the exterior environment of use. These dosage forms are designed to release drug immediately from the exterior coating, followed by a relatively short delay period, followed by a sustained release of drug from the internal compartment.

U.S. Pat. No. 4,576,604, for example, discloses an osmotic device (dosage form) comprising a drug compartment surrounded by a wall (coating) having a passageway therein. The wall may comprise an immediate release dose of drug, and the inner drug compartment may comprise a sustained release dose of drug. U.S. Pat. No. 4,449,983 discloses another osmotic device comprising two separately housed drugs that are separately dispensed from the device. The device comprises two compartments, one for each drug, separated by a partition. Each compartment has an orifice for communicating with the exterior of the device. U.S. Pat. No. 5,738,874, discloses a 3-layer pharmaceutical compressed tablet capable of liberating one or more drugs at different release rates, in which an immediate release dose of active may be contained in a compressed coating layer, and in one embodiment, the outer compressed coating layer may function via an erosion mechanism to delay release of a second dose of active ingredient contained in the core. Systems such as these are limited by the amount of drug, which may be incorporated into the exterior coating, or shell, which is in turn limited by the achievable thickness of the exterior coating or shell.

Another design for a pulsatile delivery system is exemplified in U.S. Pat. No. 4,865,849, which describes a tablet able to release active substances at successive times, comprising a first layer containing a portion of the active substance, a water soluble or water gellable barrier layer which is interposed between the first layer and a third layer containing the remaining portion of active substance, and the barrier layer and third layer are housed in an insoluble, impermeable casing. The casing can be applied by various methods such as spraying, compression, or immersion, or the tablet parts can be inserted into a pre-formed casing. Multilayer compressed tablets in stacked layer configurations necessarily require an impermeable partial coating (casing) in order to provide a pulsatile release profile. These systems suffer from the complexity and high cost of assembling multiple, separate compartments comprising multiple, different compositions.

Dosage forms have been previously designed with multiple cores housed in a single shell for the purpose of allowing flexibility in a dosing regimen. PCT Publication No. WO 00/18447, for example, describes a multiplex drug delivery system suitable for oral administration containing at least two distinct drug dosage packages, which exhibit equivalent dissolution profiles for an active agent when compared to one another and when compared to that of the entire multiplex drug delivery unit, and substantially enveloped by a scored compressed coating that allows the separation of the multiplex drug delivery system into individual drug dosage packages. In this example, a scored extended-release compartment envelops two immediate-release compartments. Active ingredient may be contained in only the extended release compartment, or additionally in the two immediate release compartments. The multiplex drug delivery systems of this example are prepared by press coating the extended-release compartment to substantially envelop the immediate release compartments.

Published U.S. patent application 2003/0235616 describes a modified release dosage form comprising at least one active ingredient and at least two cores surrounded by a shell. The shell comprises at least one opening.

Published U.S. patent application 2003/0232082 describes a modified release dosage form comprising at least one active ingredient, a core having an outer surface, and a shell that resides upon at least a portion of the core outer surface and a shell that is semi-permeable such that the liquid medium diffuses through the shell to the core due to osmosis.

Improved dosage forms for providing modified release of active ingredient are described herein. The dosage forms comprise at least one active ingredient and at least two cores surrounded by a shell, wherein the shell covers only a portion of at least one core and a fill material is provided over at least one part of the uncovered core. Upon contact with a liquid medium, active ingredient, which may be present in one or more of the cores, in the shell, or portions or combinations thereof, is released from the dosage form in a modified fashion.

SUMMARY OF THE INVENTION

The present invention relates to a medicinal dosage form having a first core, a second core, and a shell that is provided over and having a surface conforming or defining a first portion of each core. A fill material is provided over one or more cores having a surface that conform to or define a second portion of at least one core. The fill material that is provided over at least one core is not in contact with any portion of the other core. The fill material and/or the shell material can be substantially devoid of pores having a diameter of 0.5 to 5.0 microns. The first and second cores can be physically separated from one another by a section of the shell.

The fill material can extends above the surface level of the shell. The fill material can be a cap that contains an immediate release material, while the shell material is a fuse containing insoluble polymeric material. The shell can contain at least one material that is insoluble, semi-permeable, pH-dependent, or erodible in an aqueous environment.

The cores can contain a pharmaceutically active ingredient that is released immediately from the dosage form upon contacting of the dosage form with a liquid medium. Further, the shell can provide for delayed, sustained, prolonged, extended, or retarded release of at least one active ingredient contained in one or more cores. Alternatively, the active ingredient in the first core has an immediate release profile and the active ingredient in the second core has a modified release profile. Still further, a plurality of beads containing a pharmaceutically active ingredient can be formed as a core within a defined recess of the shell material.

The present invention further relates to a medicinal dosage form comprising at least one core containing a pharmaceutical active ingredient and having a cavity. At least one shell portion is provided over the core having a surface that conforms to or defines a first portion of the at least one core. A fuse material is provided in the cavity of the at least one core such that the initial release of pharmaceutical active from the core is governed by the dissolution or erosion profile of the fuse material. The shell portion or portions thereof can be insoluble in a neutral aqueous environment. Alternatively, all of the shell portion or portions thereof are soluble only when exposed to an aqueous medium having a pH greater than about 5.5 or greater than about 8. The cavity can pass entirely through a central region of the core.

The present invention also relates to a medicinal dosage form having at least one core containing a pharmaceutical active ingredient wherein a unitary shell portion is provided over the core having a surface conforming to or defining a first portion of the at least one core. A molding plug is provided in the cavity of the at least one core. The molding plug does not contain any pharmaceutical active ingredient. The core can be a compressed tablet having two opposite major faces and the unitary shell portion is provided over both major faces of the compressed tablet. One or more dimples or openings can be provided in a portion of the unitary shell that extends over the molding plug. The core can be in the shape of a torus having an open interior section and a fuse material that is in contact with a surface of the core defining the open interior section.

The present invention also relates to a medicinal dosage form having at least two cores, at least one shell portion that is provided over and having a surface conforming or defining a first portion of the cores and at least one fuse material that is provided between and in contact with at least two cores of the dosage form. In one embodiment, the fuse is exposed to a dissolution medium only upon dissolution of at least a substantial portion of at least one core in contact therewith.

The present invention also relates to methods for preparing such dosage forms. For example, one method for preparing a dosage form includes providing a shell over a first portion of a first core and a first portion of a second core, and providing a fill material over a second portion of at least one core. In another embodiment, a dosage form is prepared having a core containing a pharmaceutical active ingredient and having a cavity by providing the core with a fuse material within the cavity of the core and providing at least one shell portion having a surface conforming to a first portion of the at least one core.

In another embodiment, a dosage form can be prepared having at least core containing a pharmaceutical active ingredient by providing the core with a mold plug within the cavity of the core and providing a unitary shell portion having a surface conforming to a first portion of the core. Still further, a dosage form can be prepared having at least core containing a pharmaceutical active ingredient by providing at least one fuse material between and in contact with at least two cores of the dosage form and providing a shell portion having a surface conforming or defining a first portion of the core.

DETAILED DESCRIPTION OF THE INVENTION

Figure 1:
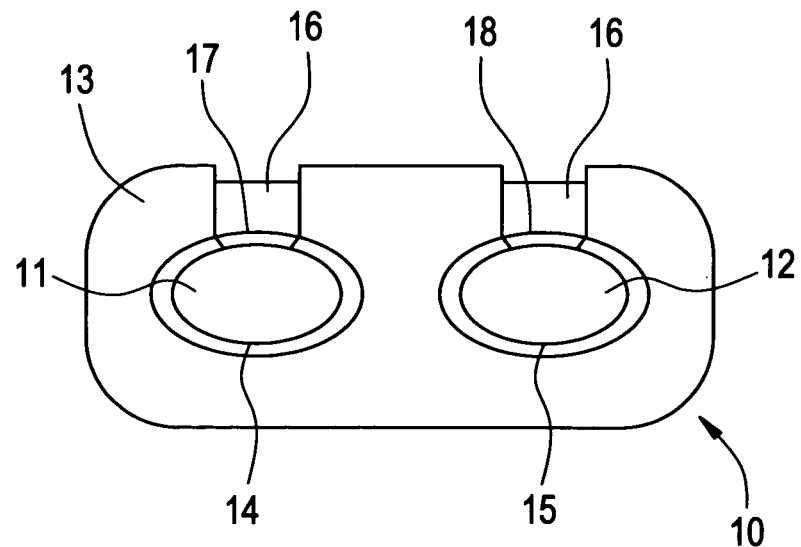
FIG. 1 illustrates an embodiment of the present invention having two cores embedded in shell material and having fill material over both cores.

As used herein, the term "dosage form" applies to any solid object, semi-solid, or liquid composition designed to contain a specific pre-determined amount (dose) of a certain ingredient, for example an active ingredient as defined below. Suitable dosage forms may be pharmaceutical drug delivery systems, including those for oral administration, buccal administration, rectal administration, topical or mucosal delivery, or subcutaneous implants, or other implanted drug delivery systems; or compositions for delivering minerals, vitamins and other nutraceuticals, oral care agents, flavorants, and the like. Preferably the dosage forms of the present invention are considered to be solid, however they may contain liquid or semi-solid components. In a particularly preferred embodiment, the dosage form is an orally administered system for delivering a pharmaceutical active ingredient to the gastro-intestinal tract of a human.

The present invention is directed to a dosage form for at least one active ingredient having a first core, a second core, and a shell that surrounds a first portion of each core and a fill material that covers a second portion of the first core and/or the second core. The fill material provided over the second portion(s) of each core are separate and distinct from the shell that is otherwise provided over the core. It is possible, however, for the fill material for either the first portion or second portion to overlap with the fill material for the other portion or to be provided in such a way as to expose the underlying core (and/or the subcoating layer). In one embodiment, either the first core or the second core is completely surrounded by or embedded in the shell material, while the remaining core is provided with a shell over a first portion and fill material over a second portion thereof. In an alternative embodiment, three or more cores are provided in the dosage form wherein none or one or more of the cores is surrounded by the shell material and at least one of the cores is only surrounded over a first portion thereof by shell material with fill material over a second portion.

In one embodiment, the shell is understood to be a material that is malleable, flowable and conformable such that a shell material, when applied, will have a surface that conforms to the shape of the element (whether a core or another underlying shell) over which it is applied. With respect to this embodiment, the core, in contrast, has a fixed, generally unitary shape that does not change significantly when introduced or provided in the dosage form. Alternatively, the shell can be molded into a desired shape suitable for holding a core or a plurality of free flowing particles that will constitute the core of the dosage form. Both of the foregoing embodiments will be characterized by having at least some fill material that is a distinct from the shell. The fill material, if it provides immediate release in a selected liquid medium, can be referred herein to as a "cap". The fill material, if it provides a delayed release of any form in a selected liquid medium, can be referred to herein as a "fuse".

An exemplary dosage form 10 is shown in FIG. 1. Dosage form 10 comprises a first core 11, a second core 12, and a shell 13. Shell 13 surrounds as one or more parts a first portion 14 of first core 11 and a first portion 15 of second core 12. Dosage form 10 can optionally be provided with a subcoating film, described more fully below, over either first core 11, second core 12 or both. Dosage form 10 is shown having fill material 16a for second portion 17 and fill material 16b for second portion 18 as non-overlapping with shell 13 and completely covering second portions 17 and 18, respectively. Non-overlapping means that fill material 16 for each of second portion 17 and second portion 18 covers the respective portions exclusively. Fill material 16 can optionally be level with, lower than, extend above and/or onto the exterior surface of shell 13. Fill material 16a and 16b can be compositionally the same or different.

Figure 2:
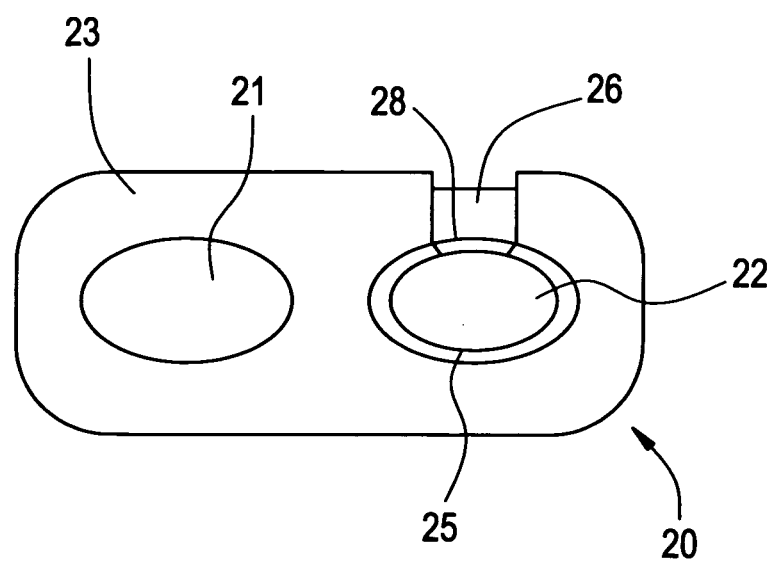
FIG. 2 illustrates an alternative embodiment having two cores embedded in shell material and having fill material only over one core.

An alternative dosage form 20 is shown in FIG. 2. Alternative dosage form 20 comprises a first core 21, a second core 22, and a shell 23. Shell 23 surrounds all of first core 21 and a first portion 25 of second core 22. Fill material 26 covers a second portion 28 of second core 22. Dosage form 20 can optionally be provided with a subcoating film over either first core 21, second core 22 or both. Dosage form 20 is shown having fill material 26a for second portion 28 as non-overlapping with shell 23 and completely covering second portion 28. Fill material 26s can optionally be level with, lower than, extend above and/or onto the exterior surface of shell 23.

Figure 3:
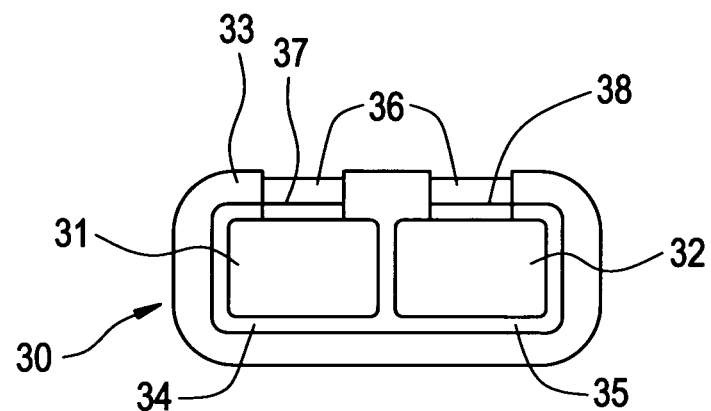
FIG. 3 illustrates an embodiment of the present invention in which fill material is provided between and in contact with two cores.

An alternative dosage form 30 is shown in FIG. 3. Dosage form 30 comprises a first core 31, a second core 32, and a shell 33. Shell 33 surrounds as one or more parts a first portion 34 of first core 31 and a first portion 35 of second core 32. Dosage form 30 can optionally be provided with a subcoating film over either first core 31, second core 32 or both. Dosage form 30 is shown having fill material 36a for second portion 37 and fill material 36b for second portion 38 as non-overlapping with shell 33 and completely covering second portions 37 and 38, respectively. The primary difference relative to dosage form 10 is the positioning of first core 31 and second 31 and the incorporation of a fill material 36c between the two cores. Fill material 36a and 36b can optionally be level with, lower than, extend above and/or onto the exterior surface of shell 33. Fill material 36a, 36b and 36c can be compositionally the same or different.

Figure 4:
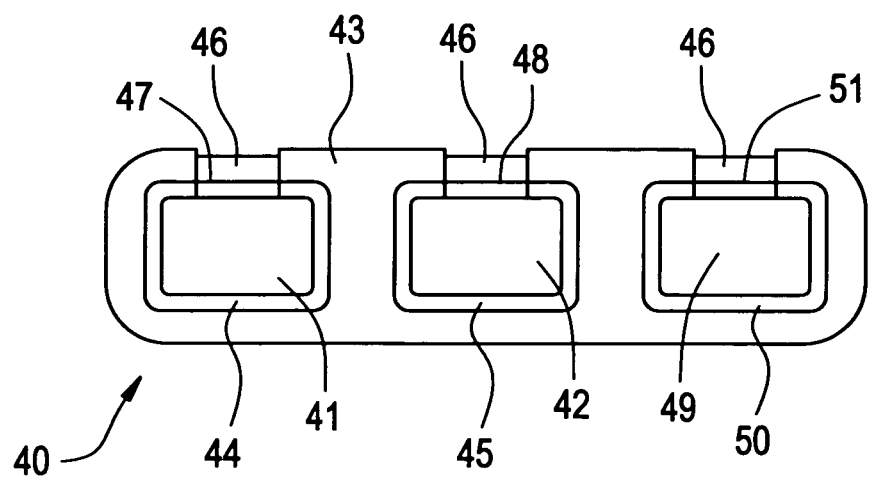
FIG. 4 illustrates an alternative embodiment having three cores.

An exemplary dosage form 40 is shown in FIG. 4. Dosage form 40 comprises a first core 41, a second core 42, third core 49 and a shell 43. Shell 43 surrounds as one or more parts a first portion 44 of first core 41, a first portion 45 of second core 42 and a first portion 50 of third core 49. Fill material 46a covers a second portion 47 of first core 41, fill material 46b covers a second portion 48 of second core 42 and fill material 46c covers a second portion 51 of third core 49. Dosage form 40 can optionally be provided with a subcoating film over any or all of first core 41, second core 42 and third core 49. Fill material 46 can optionally be level with, lower than, extend above and/or onto the exterior surface of shell 43. Fill material 46a, 46b and 46c can be compositionally the same or different. Still further embodiments are possible in which two or more cores are provided adjacent to one another or connected via a fill material in a manner similar to dosage form 30.

The active ingredient or ingredients are present in the dosage form in a therapeutically effective amount, which is an amount that produces the desired therapeutic response upon oral administration and can be readily determined by one skilled in the art. In determining such amounts, the particular active ingredient being administered, the bioavailability characteristics of the active ingredient, the dosing regimen, the age and weight of the patient, and other factors must be considered, as known in the art. Typically, the dosage form comprises at least about 1 weight percent, for example, the dosage form comprises at least about 5 weight percent, say at least about 20 weight percent of a combination of one or more active ingredients. In one embodiment, a core comprises a total of at least about 25 weight percent (based on the weight of the core) of one or more active ingredients.

The active ingredient or ingredients may be present in the dosage form in any form. For example, the active ingredient may be dispersed at the molecular level, e.g. melted or dissolved, within the dosage form, or may be in the form of particles, which in turn may be coated or uncoated. If an active ingredient is in the form of particles, the particles (whether coated or uncoated) typically have an average particle size of about 1-2000 microns.

Each core may be any solid form. As used herein, "core" refers to a material that is at least partially enveloped or surrounded by another material. Preferably, a core is a self-contained unitary object, such as a tablet or capsule. Typically, a core comprises a solid, for example, a core may be a compressed or molded tablet, hard or soft capsule, suppository, or a confectionery form such as a lozenge, nougat, caramel, fondant, or fat based composition or an osmotic capsule. In certain other embodiments, a core or a portion thereof may be in the form of a semi-solid or a liquid in the finished dosage form. For example a core may comprise a liquid filled capsule, or a semisolid fondant material. In embodiments in which a core comprises a flowable component, such as a plurality of granules or particles, or a liquid, the core preferably additionally comprises an enveloping component, such as a capsule shell, or a molded coating, for containing the flowable material. In certain particular embodiments in which a core comprises an enveloping component, the shell or shell portions of the present invention are in direct contact with the enveloping component of the core, which separates the shell from the flowable component of the core.

One or more of the cores is provided with, as by being surrounded or partially covered by, or embedded in, the shell over at least a first portion of said cores. In one embodiment, the first and second cores are in physical contact with one another. The term "surrounded", for purposes of this application, is not meant to imply that all surfaces must be covered by the same shell or other coating material. A core can be partially covered by an overcoated shell material while some of the core is exposed to the external environment. The term is intended to convey the concept of the shell material being provided in a flowable condition so as to conform to the surface of the underlying element. Alternatively, a portion or section of shell, referred herein as the "interior wall" separates one or more cores. The distance between the cores, i.e. thickness of the interior wall may vary depending upon the desired release characteristics of the dosage form, or practical considerations related to the manufacturing process. In certain embodiments, the distance between the cores within the dosage form, i.e. the thickness of the interior wall, is on the order of the thickness of the shell proximal to the core. For example, the thickness of the interior wall may be from about 10% to about 200% of the thickness of a core.

The core may have one of a variety of different shapes. Each core may have the same or different physical dimensions, shape, etc. as the other cores. In certain embodiments, a core has one or more major faces. For example, in embodiments wherein a core is a compressed tablet, the core surface typically has opposing upper and lower faces formed by contact with the upper and lower punch faces in the compression machine. In such embodiments the core surface typically further comprises a "belly-band" located between the upper and lower faces, and formed by contact with the die walls in the compression machine. A core may also comprise a multilayer tablet.

In one embodiment at least one core is a compressed tablet having a hardness from about 2 to about 30 kp/cm$^2$, e.g. from about 6 to about 25 kp/cm$^2$. "Hardness" is a term used in the art to describe the diametral breaking strength of either the core or the coated solid dosage form as measured by conventional pharmaceutical hardness testing equipment, such as a Schleuniger Hardness Tester. In order to compare values across different size tablets, the breaking strength must be normalized for the area of the break. This normalized value, expressed in kp/cm$^2$, is sometimes referred in the art as tablet tensile strength. A general discussion of tablet hardness testing is found in Leiberman et al., *Pharmaceutical Dosage Forms—Tablets*, Volume 2, 2$^{nd}$ ed., Marcel Dekker Inc., 1990, pp. 213-217, 327-329. In another embodiment, all the cores in the dosage form comprise a compressed tablet having a hardness from about 2 to about 30 kp/cm$^2$, e.g. from about 6 to about 25 kp/cm$^2$.

Exemplary core shapes that may be employed include tablet shapes formed from compression tooling shapes described by "The Elizabeth Companies Tablet Design Training Manual" (Elizabeth Carbide Die Co., Inc., p. 7 (McKeesport, Pa.) (incorporated herein by reference). The cores may be prepared by any suitable method, including for example compression or molding, and depending on the method by which they are made, typically comprise active ingredient and a variety of excipients.

In embodiments in which one or more cores, or portions thereof are made by compression, suitable excipients include fillers, binders, disintegrants, lubricants, glidants, and the like, as known in the art. In embodiments in which a core is made by compression and additionally confers modified release of an active ingredient contained therein, such core preferably further comprises a release-modifying compressible excipient.

Suitable fillers for use in making a core or core portion by compression include water-soluble compressible carbohydrates such as sugars, which include dextrose, sucrose, maltose, and lactose, sugar-alcohols, which include mannitol, sorbitol, maltitol, xylitol, starch hydrolysates, which include dextrins, and maltodextrins, and the like, water insoluble plastically deforming materials such as microcrystalline cellulose or other cellulosic derivatives, water-insoluble brittle fracture materials such as dicalcium phosphate, tricalcium phosphate and the like and mixtures thereof.

Suitable binders for making a core or core portion by compression include dry binders such as polyvinyl pyrrolidone, hydroxypropylmethylcellulose, and the like; wet binders such as water-soluble polymers, including hydrocolloids such as acacia, alginates, agar, guar gum, locust bean, carrageenan, carboxymethylcellulose, tara, gum arabic, tragacanth, pectin, xanthan, gellan, gelatin, maltodextrin, galactomannan, pusstulan, laminarin, scleroglucan, inulin, whelan, rhamsan, zooglan, methylan, chitin, cyclodextrin, chitosan, polyvinyl pyrrolidone, cellulosics, sucrose, starches, and the like; and derivatives and mixtures thereof.

Suitable disintegrants for making a core or core portion by compression, include sodium starch glycolate, cross-linked polyvinylpyrrolidone, cross-linked carboxymethylcellulose, starches, microcrystalline cellulose, and the like. Suitable lubricants for making a core or core portion by compression include long chain fatty acids and their salts, such as magnesium stearate and stearic acid, talc, glycerides and waxes. Suitable glidants for making a core or core portion by compression, include colloidal silicon dioxide, and the like. Suitable release-modifying excipients for making a core or core portion by compression include swellable erodible hydrophilic materials, insoluble edible materials, pH-dependent polymers, and the like.

Suitable swellable erodible hydrophilic materials for use as release-modifying excipients for making a core or core portion by compression include: water swellable cellulose derivatives, polyalkylene glycols, thermoplastic polyalkylene oxides, acrylic polymers, hydrocolloids, clays, gelling starches, and swelling cross-linked polymers, and derivatives, copolymers, and combinations thereof. Examples of suitable water swellable cellulose derivatives include sodium carboxymethylcellulose, cross-linked hydroxypropylcellulose, hydroxypropyl cellulose (HPC), hydroxypropylmethylcellulose (HPMC), hydroxyisopropylcellulose, hydroxybutylcellulose, hydroxyphenylcellulose, hydroxyethylcellulose (HEC), hydroxypentylcellulose, hydroxypropylethylcellulose, hydroxypropylbutylcellulose, hydroxypropylethylcellulose. Examples of suitable polyalkylene glycols include polyethylene glycol. Examples of suitable thermoplastic polyalkylene oxides include poly(ethylene oxide). Examples of suitable acrylic polymers include potassium methacrylate divinylbenzene copolymer, polymethylmethacrylate, CARBOPOL (high-molecular weight cross-linked acrylic acid homopolymers and copolymers), and the like. Examples of suitable hydrocolloids include alginates, agar, guar gum, locust bean gum, kappa carrageenan, iota carrageenan, tara, gum arabic, tragacanth, pectin, xanthan gum, gellan gum, maltodextrin, galactomannan, pusstulan, laminarin, scleroglucan, gum arabic, inulin, pectin, gelatin, whelan, rhamsan, zooglan, methylan, chitin, cyclodextrin, chitosan. Examples of suitable clays include smectites such as bentonite, kaolin, and laponite; magnesium trisilicate, magnesium aluminum silicate, and the like, and derivatives and mixtures thereof. Examples of suitable gelling starches include acid hydrolyzed starches, swelling starches such as sodium starch glycolate, and derivatives thereof. Examples of suitable swelling cross-linked polymers include cross-linked polyvinyl pyrrolidone, cross-linked agar, and cross-linked carboxymethylcellulose sodium.

Suitable insoluble edible materials for use as release-modifying excipients for making a core or core portion by compression include water-insoluble polymers, and low-melting hydrophobic materials. Examples of suitable water-insoluble polymers include ethylcellulose, polyvinyl alcohols, polyvinyl acetate, polycaprolactones, cellulose acetate and its derivatives, acrylates, methacrylates, acrylic acid copolymers; and the like and derivatives, copolymers, and combinations thereof. Suitable low-melting hydrophobic materials include fats, fatty acid esters, phospholipids, and waxes. Examples of suitable fats include hydrogenated vegetable oils such as for example cocoa butter, hydrogenated palm kernel oil, hydrogenated cottonseed oil, hydrogenated sunflower oil, and hydrogenated soybean oil; and free fatty acids and their salts. Examples of suitable fatty acid esters include sucrose fatty acid esters, mono, di, and triglycerides, glyceryl behenate, glyceryl palmitostearate, glyceryl monostearate, glyceryl tristearate, glyceryl trilaurylate, glyceryl myristate, GlycoWax-932, lauroyl macrogol-32 glycerides, and stearoyl macrogol-32 glycerides. Examples of suitable phospholipids include phosphotidyl choline, phosphotidyl serene, phosphotidyl enositol, and phosphotidic acid. Examples of suitable waxes include carnauba wax, spermaceti wax, beeswax, candelilla wax, shellac wax, microcrystalline wax, and paraffin wax; fat-containing mixtures such as chocolate; and the like.

Suitable pH-dependent polymers for use as release-modifying excipients for making a core or core portion by compression include enteric cellulose derivatives, for example hydroxypropyl methylcellulose phthalate, hydroxypropyl methylcellulose acetate succinate, cellulose acetate phthalate; natural resins such as shellac and zein; enteric acetate derivatives such as for example polyvinylacetate phthalate, cellulose acetate phthalate, acetaldehyde dimethylcellulose acetate; and enteric acrylate derivatives such as for example polymethacrylate-based polymers such as poly(methacrylic acid, methyl methacrylate) 1:2, which is commercially available from Rohm Pharma GmbH under the tradename EUDRAGIT S, and poly(methacrylic acid, methyl methacrylate) 1:1, which is commercially available from Rohm Pharma GmbH under the tradename EUDRAGIT L, and the like, and derivatives, salts, copolymers, and combinations thereof.

Suitable pharmaceutically acceptable adjuvants for making a core or core portion by compression include, preservatives; high intensity sweeteners such as aspartame, acesulfame potassium, sucralose, and saccharin; flavorants; colorants; antioxidants; surfactants; wetting agents; and the like and mixtures thereof.

In embodiments wherein one or more cores are prepared by compression, a dry blending (i.e. direct compression), or wet granulation process may be employed, as known in the art. In a dry blending (direct compression) method, the active ingredient or ingredients, together with the excipients, are blended in a suitable blender, than transferred directly to a compression machine for pressing into tablets. In a wet granulation method, the active ingredient or ingredients, appropriate excipients, and a solution or dispersion of a wet binder (e.g. an aqueous cooked starch paste, or solution of polyvinyl pyrrolidone) are mixed and granulated. Alternatively a dry binder may be included among the excipients, and the mixture may be granulated with water or other suitable solvent. Suitable apparatuses for wet granulation are known in the art, including low shear, e.g. planetary mixers; high shear mixers; and fluid beds, including rotary fluid beds. The resulting granulated material is dried, and optionally dry-blended with further ingredients, e.g. adjuvants and/or excipients such as for example lubricants, colorants, and the like. The final dry blend is then suitable for compression. Methods for direct compression and wet granulation processes are known in the art, and are described in detail in, for example, Lachman, et al., *The Theory and Practice of Industrial Pharmacy*, Chapter 11 ($3^{rd}$ ed. 1986).

The dry-blended, or wet granulated, powder mixture is typically compacted into tablets using a rotary compression machine as known in the art, such as for example those commercially available from Fette America Inc., Rockaway, N.J., or Manesty Machines LTD, Liverpool, UK. In a rotary compression machine, a metered volume of powder is filled into a die cavity, which rotates as part of a "die table" from the filling position to a compaction position where the powder is compacted between an upper and a lower punch to an ejection position where the resulting tablet is pushed from the die cavity by the lower punch and guided to an ejection chute by a stationary "take-off" bar.

In one embodiment, at least one core is prepared by the compression methods and apparatus described in copending U.S. Pat. No. 6,767,200, the disclosure of which is incorporated herein by reference. Specifically, the core is made using a rotary compression module comprising a fill zone, compression zone, and ejection zone in a single apparatus having a double row die construction as shown in FIG. 6 of U.S. Pat. No. 6,767,200. The dies of the compression module are preferably filled using the assistance of a vacuum, with filters located in or near each die. Cores made by compression may be single or multi-layer, for example bi-layer, tablets.

In another embodiment the core is made up of a plurality of beads that contain at least one active ingredient. A mixture of beads having different active ingredients can be utilized in the dosage form. These beads may be coated with a release modifying agent in order to affect the dissolution characteristics of the active ingredient. The beads may also be coated with a polymer to protect the active ingredient from interaction with other active ingredients, the shell or the fill material. The beads may be placed into the dosage form as a previously compressed unitary mass, or filled as loosely separated beads into a core cavity previously molded into the surrounding shell.

The beads can be prepared by coating a drug active onto an inert substrate, e.g., non-pareil seeds, then optionally further coated with a release-modifying coating in conventional fashion using a fluidized bed. Alternatively, the beads can be in the form of granulated particles formed by high shear, spray fluid bed or rotor-granulator processes. Such granulated particles can optionally have a release-modifying coating that can be accomplished in conventional fashion using a fluidized bed. Still further, the beads can be prepared as spray dried particles, which then can optionally be further coated with a release-modifying coating in a fluidized bed.

If the beads are in form of particles, the particles (whether coated or uncoated) typically have an average particle size of about 1 to about 2000 microns. In another preferred embodiment, the particles are granules or pellets having an average particle size of about 50 to about 2000 microns, preferably about 50 to about 1000 microns, most preferably about 100 to about 800 microns.

In particular embodiments of this invention in which coated particles are employed, the particles may be as described herein, and the particle coating may comprise about 10 to 100 weight percent (based on the weight of the coating) of a film former; optionally up to about 50 weight percent based on the weight of the coating of a pore former; and optionally up to about 30 weight percent of various adjuvants or excipients such as plasticizers etc. The particles may be coated using conventional coating technology which is well known to those skilled in the art including microencapsulation techniques such as coacervation, spray-drying, and fluidized bed coating including tangential spray rotor coating and bottom spray wurster coating. Examples of suitable particle coating methods and materials can be found in U.S. Pat. Nos. 5,286,497; 4,863,742; 4,173,626; 4,980,170; 4,984,240; 5,912,013; 6,270,805; and 6,322,819. Such coated particles may provide controlled release of the active ingredient contained therein in certain embodiments.

Suitable film formers for particle coating include, but are not limited to, film-forming water soluble polymers, film-forming proteins, film-forming water insoluble polymers, and film-forming pH-dependent polymers. In one embodiment, the film-former for particle coating may be selected from cellulose acetate, ammonio methacrylate copolymer type B, shellac, hydroxypropylmethylcellulose, and polyethylene oxide, and combinations thereof.

In embodiments in which the particle coating confers modified release to one or more active ingredients contained in the particle, suitable film formers may be selected from film forming water insoluble polymers; film forming pH-dependent polymers; and copolymers and combinations thereof. In certain such embodiments in which the particle coating functions as a diffusional membrane, the release-modifying particle coating preferably comprises a pore former. In certain embodiments the dosage form comprises multiple shell portions that are compositionally different. Additionally, the shell and fill material will preferably be compositionally and functionally different.

As used herein, the term "compositionally different" means having features that are readily distinguishable by qualitative or quantitative chemical analysis, physical testing, or visual observation. For example, the first and second shell portions may contain different ingredients, or different levels of the same ingredients, or the first and second shell portions may have different physical or chemical properties, different functional properties, or be visually distinct. Examples of physical or chemical properties that may be different include hydrophylicity, hydrophobicity, hygroscopicity, elasticity, plasticity, tensile strength, crystallinity, and density. Examples of functional properties which may be different include rate and/or extent of dissolution of the material itself or of an active ingredient therefrom, rate of disintegration of the material, permeability to active ingredients, permeability to water or aqueous media, and the like. Examples of visual distinctions include size, shape, topography, or other geometric features, color, hue, opacity, and gloss.

In one embodiment, one core can be in the form of a solid solution, containing active ingredient in the amorphous state. The dosage form of this invention allows for separation of one active in the amorphous state in one core and one active in the crystalline state in a second core. In another embodiment, two active ingredients that are incompatible are separated into their respective cores, and are released simultaneously upon dissolution of the fill material, providing a synergistic therapeutic effect. An example of this would be a combination therapy for the treatment of the human immunodeficiency (HIV) virus, where two protease enzyme inhibitors are combined into one core and one nucleoside enzyme inhibitor is combined into a separate core. Another example includes the combination of one ACE (angiotensin converting enzyme) inhibitor in one core plus another ACE inhibitor in another core for use as therapy for hypertension.

In one embodiment, the fill material is an immediate release material and one or more sections of the shell are enteric materials or impermeable to neutral aqueous systems at room temperature. Alternatively, the shell can provide for delayed, sustained, prolonged, extended, or retarded release of at least one active ingredient contained in one core, while the fill material is provided over one or more of the remaining cores having an immediate release profile. The shell may also be semi-permeable, where water is allowed to flow into the core portion or portions in one direction. Still further, the shell can be impermeable to neutral aqueous systems at room temperature while the fill material can be provided having a delayed, sustained, prolonged, extended, or retarded release of at least one active ingredient from the core, each of the fill materials having the same or different release profiles from one another.

In other embodiments the composition of the fill materials may function to modify the release of an active ingredient contained in one or more of the underlying cores. In one embodiment, the fill material may function to delay release of an active ingredient from at least one underlying core. In another embodiment, the fill material may function to sustain, extend, retard, or prolong the release of at least one active ingredient from at least one core. The foregoing embodiments can be combined into a single dosage form.

In certain embodiments, the fill material comprises release modifying moldable excipients, such as, but not limited to, swellable erodible hydrophilic materials, insoluble edible materials, pH dependent polymers, clays, gelling starches, cross-linked polymers and pharmaceutically acceptable adjuvants described above.

In certain embodiments, the fill material itself, e.g. a portion thereof, may also contain active ingredient. In one embodiment, such active ingredient will be released immediately from the dosage form upon ingestion, or contacting of the dosage form with a liquid medium. In another embodiment, such active ingredient will be released in a controlled, sustained, prolonged, or extended fashion upon ingestion, or contacting of the dosage form with a liquid medium. The foregoing embodiments can be combined into a single dosage form. Similarly, combinations of the fill material, with and without active ingredients can be envisioned that are combined with fill materials having different release profiles.

In a further embodiment, the fill material can be provided entirely within and through a cavity of an active containing core. This embodiment can be suitable for producing a dosage form having a unitary shell coating that is produced in a single shot injection molding system. The fill material can act as a form of a support or molding plug upon which supports retain the combination within an injection molding cavity and allow shell material to coat the core and molding plug. The molded shell coating can be textured, dimpled or even have further openings to expose the underlying core. The term "unitary" is meant to describe a molded shell coated that does not have any seams. The shell in such a case would preferably be dissolvable in an appropriate liquid medium, and further preferably would control the release profile of the active contained in the core.

The use of subcoatings is well known in the art and disclosed in, for example, U.S. Pat. No. 3,185,626, which is incorporated by reference herein. Any composition suitable for film-coating a tablet may be used as a subcoating according to the present invention. Examples of suitable subcoatings are disclosed in U.S. Pat. Nos. 4,683,256, 4,543,370, 4,643,894, 4,828,841, 4,725,441, 4,802,924, 5,630,871, and 6,274,162, which are all incorporated by reference herein. Additional suitable subcoatings include one or more of the following ingredients: cellulose ethers such as hydroxypropylmethylcellulose, hydroxypropylcellulose, and hydroxyethylcellulose; polycarbohydrates such as xanthan gum, starch, and maltodextrin; plasticizers including for example, glycerin, polyethylene glycol, propylene glycol, dibutyl sebecate, triethyl citrate, vegetable oils such as castor oil, surfactants such as Polysorbate-80, sodium lauryl sulfate and dioctyl-sodium sulfosuccinate; polycarbohydrates, pigments, and opacifiers.

In one embodiment, the subcoating comprises, based upon the total weight of the subcoating, from about 2 percent to about 8 percent, e.g. from about 4 percent to about 6 percent of a water-soluble cellulose ether and from about 0.1 percent to about 1 percent, castor oil, as disclosed in detail in U.S. Pat. No. 5,658,589, which is incorporated by reference herein. In another embodiment, the subcoating comprises, based upon the total weight of the subcoating, from about 20 percent to about 50 percent, e.g., from about 25 percent to about 40 percent of HPMC; from about 45 percent to about 75 percent, e.g., from about 50 percent to about 70 percent of maltodextrin; and from about 1 percent to about 10 percent, e.g., from about 5 percent to about 10 percent of PEG 400.

In embodiments in which a subcoating is employed, the dried subcoating typically is present in an amount, based upon the dry weight of the core, from about 0 percent to about 5 percent. In another embodiment, one or more cores, e.g. all the cores, are substantially free of subcoating, and the shell or a shell portion is in direct contact with a core surface.

The dosage forms of the invention provide modified release of one or more active ingredients contained therein. The active ingredient or ingredients may be found within one or more cores, the shell, the fill materials or portions or combinations thereof. Preferably, one or more active ingredients are contained in one or more cores. More preferably, at least one active ingredient is contained in each of the cores.

The shell, or a portion thereof can provide for a modified release of at least one active ingredient in the dosage form. As used herein, the term "modified release" means the release of an active ingredient from a dosage form or a portion thereof in other than an immediate release fashion, i.e., other than immediately upon contact of the dosage form or portion thereof with a liquid medium. "Modified release" can be evidenced by modified dissolution characteristics. As known in the art, types of modified release include delayed or controlled. Types of controlled release include pH dependent, prolonged, sustained, extended, retarded, and the like. Modified release profiles that incorporate a delayed release feature include pulsatile, repeat action, and the like. As is also known in the art, suitable mechanisms for achieving modified release of an active ingredient include diffusion, erosion, surface area control via geometry and/or impermeable barriers, semi-permeable barriers and other known mechanisms known.

In a preferred embodiment, at least one active ingredient is released from the first core in an immediate release fashion. As used herein, "immediate release" means the dissolution characteristics of an active ingredient meets USP specifications for immediate release tablets containing the active ingredient. For example, for acetaminophen tablets, USP 24 specifies that in pH 5.8 phosphate buffer, using USP apparatus 2 (paddles) at 50 rpm, at least 80% of the acetaminophen contained in the dosage form is released therefrom within 30 minutes after dosing, and for ibuprofen tablets, USP 24 specifies that in pH 7.2 phosphate buffer, using USP apparatus 2 (paddles) at 50 rpm, at least 80% of the ibuprofen contained in the dosage form is released therefrom within 60 minutes after dosing. See USP 24, 2000 Version, 19-20 and 856 (1999).

The composition of the shell may function to modify the release there through of an active ingredient contained in an underlying core. In one embodiment, the shell may function to delay release of an active ingredient from an underlying core. In another embodiment, the shell may function to sustain, extend, retard, or prolong the release of at least one active ingredient from the second (distally located) core.

In one embodiment, the shell comprises a release modifying moldable excipient, such as, but not limited to, swellable erodible hydrophilic materials described above.

In another embodiment, the dosage form is substantially free (i.e. less than 1% by weight, preferably less than about 0.1% by weight, based upon the shell weight) of charge control agents. As used herein, the term "charge control agents" refers to a material having a charge control function, such as those used for electrostatic deposition of coatings onto substrates. Such charge control agents include metal salicylates, for example zinc salicylate, magnesium salicylate and calcium salicylate; quaternary ammonium salts; benzalkonium chloride; benzethonium chloride; trimethyl tetradecyl ammonium bromide (cetrimide); and cyclodextrins and their adducts.

In a second preferred embodiment such as described in the preceding paragraphs, one or more active ingredients contained in the second core are released in a controlled, sustained, prolonged, or extended manner beginning initially upon contact of the dosage for with a liquid medium, without a substantial preceding lag time, e.g. release of at least one active ingredients begins within 30 minutes, e.g. within 15 minutes, say within 10 minutes, of contact of the dosage form with a liquid medium.

In certain embodiments, the shell itself, e.g. a portion thereof, or an outer coating thereon may also contain active ingredient. In one embodiment, such active ingredient will be released immediately from the dosage form upon ingestion, or contacting of the dosage form with a liquid medium. In another embodiment, such active ingredient will be released in a controlled, sustained, prolonged, or extended fashion upon ingestion, or contacting of the dosage form with a liquid medium.

In certain preferred embodiments of the invention, the cores, the shell, any portions thereof and/or fill material are prepared by molding. In particular, the cores, the shell, the fill material or all may be made by solvent-based molding or solvent-free molding. In such embodiments, the core or the shell is made from a flowable material optionally comprising active ingredient. The flowable material may be any edible material that is flowable at a temperature between about 37° C. and 250° C., and that is solid, semi-solid, or can form a gel at a temperature between about −10° C. and about 35° C. When it is in the fluid or flowable state, the flowable material may comprise a dissolved or molten component for solvent-free molding, or optionally a solvent such as for example water or organic solvents, or combinations thereof, for solvent-based molding. The solvent may be partially or substantially removed by drying.

In one embodiment, solvent-based or solvent-free molding is performed via thermal setting molding using the method and apparatus described in published U.S. patent application 2003-0124183, the disclosure of which is incorporated herein by reference. In this embodiment, a core or shell is formed by injecting flowable form into a molding chamber. The flowable material preferably comprises a thermal setting material at a temperature above its melting point but below the decomposition temperature of any active ingredient contained therein. The flowable material is cooled and solidifies in the molding chamber into a shaped form (i.e., having the shape of the mold).

According to this method, the flowable material may comprise solid particles suspended in a molten matrix, for example a polymer matrix. The flowable material may be completely molten or in the form of a paste. The flowable material may comprise an active ingredient dissolved in a molten material in the case of solvent-free molding. Alternatively, the flowable material may be made by dissolving a solid in a solvent, which solvent is then evaporated after the molding step in the case of solvent-based molding.

In another embodiment, solvent-based or solvent-free molding is performed by thermal cycle molding using the method and apparatus described in published U.S. patent application US 2003-0086973, the disclosure of which is incorporated herein by reference. Thermal cycle molding is performed by injecting a flowable material into a heated molding chamber. The flowable material may comprise active ingredient and a thermoplastic material at a temperature above the set temperature of the thermoplastic material but below the decomposition temperature of active ingredient. The flowable material is cooled and solidifies in the molding chamber into a shaped form (i.e., having the shape of the mold).

In the thermal cycle molding method and apparatus of published U.S. patent application US 2003-0086973 a thermal cycle molding module having the general configuration shown in FIG. 3 therein is employed. The thermal cycle molding module comprises a rotor around which a plurality of mold units are disposed. The thermal cycle molding module includes a reservoir for holding flowable material to make the core. In addition, the thermal cycle molding module is provided with a temperature control system for rapidly heating and cooling the mold units.

The mold units may comprise center mold assemblies, upper mold assemblies, and lower mold assemblies that mate to form mold cavities having a desired shape, for instance of a core or a shell surrounding one or more cores. As rotor rotates, opposing center and upper mold assemblies or opposing center and lower mold assemblies close. Flowable material, which is heated to a flowable state in reservoir, is injected into the resulting mold cavities. The temperature of the flowable material is then decreased, hardening the flowable material. The mold assemblies open and eject the finished product.

In one embodiment of the invention, the shell is applied to the dosage form using a thermal cycle molding apparatus of the general type of published U.S. application US 2003-0086973 comprising rotatable center mold assemblies, lower mold assemblies and upper mold assemblies. Cores are continuously fed to the mold assemblies. Shell flowable material, which is heated to a flowable state in reservoir, is injected into the mold cavities created by the closed mold assemblies holding the cores. The temperature of the shell flowable material is then decreased, hardening it around the cores. The mold assemblies open and eject the finished dosage forms. Shell coating is performed in two steps, each half of the dosage forms being coated separately as shown in the flow diagram published U.S. patent application 2003-0068367 via rotation of the center mold assembly.

In particular, the mold assemblies for applying the shell are provided with two or more cavities to accommodate the desired number of cores in the dosage form. A wall, preferably made of rubber or metal, separates the cavities and the overall shape of the cavities conform to the shape of the cores.

In one embodiment of the invention, the shell is applied to the dosage form using a zero cycle molding apparatus of the general type of copending application Ser. No. 10/677,984, filed Oct. 2, 2003 (MCP5018), which is incorporated herein by reference, comprising rotatable center mold assemblies, lower mold assemblies and upper mold assemblies. Cores are continuously fed to the mold assemblies. Shell flowable material, which is heated to a flowable state in reservoir, is injected into the mold cavities created by the closed mold assemblies holding the cores. The mold assemblies open and eject the finished dosage forms. Shell coating is preferably performed in two steps, each half of the dosage forms being coated separately via rotation of the center mold assembly.

In particular, the mold assemblies for applying the shell are provided with two or more cavities to accommodate the desired number of cores in the dosage form. A wall, preferably made of rubber or metal, separates the cavities and the overall shape of the cavities conform to the shape of the cores.

In one embodiment, the compression module of U.S. Pat. No. 6,767,200 may be employed to make cores. The shell may be made applied to these cores using a thermal cycle molding module as described above. A transfer device may be used to transfer the cores from the compression module to the thermal cycle molding module. Such a transfer device may have the structure shown published U.S. patent application 2003-0068367. It comprises a plurality of transfer units attached in cantilever fashion to a belt. The transfer device rotates and operates in sync with the compression module and the thermal cycle molding module to which it is coupled. Transfer units comprise retainers for holding cores as they travel around the transfer device.

Each transfer unit comprises multiple retainers for holding multiple cores side by side. In one embodiment, the distance between the retainers within each transfer unit is adjusted via a cam track/cam follower mechanism as the transfer units move around the transfer device. On arrival at the selected molding module, the cores grouped together for placement in a single dosage form, which have been held within a single transfer unit, are properly spaced from one another and ready to be fed into the mold assemblies. The cores may or may not have the same composition, as desired. The cores may comprise a single layer or multiple layers.

Alternatively, if cores of the same composition are to be used in the dosage forms, the compression module may be equipped with multi-tip compression tooling. Three or four-tip tooling, for example, may be used to make three or four cores within one die. The cores may comprise a single layer or multiple layers.

In certain preferred embodiments the dosage form is made using a modification of the apparatus shown in copending U.S. application Ser. No. 09/966,497, which is incorporated herein by reference. In one embodiment the shell material and fill material are applied to the dosage form by holding the core tablet by one or more prongs. At the beginning of the molding cycle (rotor at the 0 degree position) the mold assemblies are in the open position. Center mold assembly 212 as shown in copending U.S. application Ser. No. 09/966,497 as incorporated herein by reference, has received the compressed cores, for example from a compression module according to the invention transferred via a transfer device also according to the invention. As the rotor continues to revolve, the cores are held in the upper mold assembly 214 by one or more prongs surrounded by a gasket, on one portion of the cores. The upper mold assembly closes against the center mold assembly 212. The gasket containing the prongs allows for a portion of the cores to remain uncoated by the shell. Next, flowable material is injected into the mold cavity created by union of the mold assemblies to apply the shell to the cores. The flowable shell material is cooled in the mold cavity. The mold assemblies open with the cores remaining in the upper mold assembly 214. Upon further revolution of the rotor, the center mold assembly rotates 180 degrees. As the rotor moves past 180 degrees the dosage forms are removed from the gasket and the mold assemblies again close and the portion of the dosage forms which were previously uncoated are covered with flowable fill material to form the fill portion 16 as shown in FIG. 1 of the dosage forms. A molding cycle is completed with setting or hardening of the fill materials. The mold assemblies again open and the coated compressed dosage form is ejected from the thermal cycle molding module.

In certain preferred embodiments the dosage form is made using a modification of the apparatus shown in copending U.S. application Ser. No. 09/966,497. In one embodiment, the shell and fill materials are applied to the dosage form by injecting the shell in two steps, followed by injection of the fill materials. At the beginning of the molding cycle (rotor at the 0 degree position) the mold assemblies are in the open position. Center mold assembly 212 as shown in copending U.S. application Ser. No. 09/966,497 as incorporated herein by reference, has received the compressed cores, for example from a compression module according to the invention transferred via a transfer device also according to the invention. As the rotor continues to revolve, the upper mold assembly 214 closes against center mold assembly 212. Next, flowable material is injected into the mold cavity created by union of the mold assemblies to apply a shell to the first half of the dosage form. The flowable material is cooled in the mold cavity. The mold assemblies open with the partially coated dosage forms remaining in the upper mold assembly 214. Upon further revolution of the rotor, the center mold assembly rotates 180 degrees. As the rotor moves past 180 degrees the mold assemblies again close and the uncoated portion of the compressed dosage form is covered with flowable material thus forming a shell having an opening aligned with the fill material, in a mold assembly that contains one or more protrusions which prevent a portion of the cores from being covered. The protrusion also contains a nozzle for injecting the fill material. The protrusion retracts following the application of the second portion of the shell, and the flowable fill material is injected into the uncoated portion of the dosage form, forming the fill portion 16 as shown in FIG. 1. A molding cycle is completed with setting or hardening of the shell and fill materials on the second half of the compressed dosage form. The mold assemblies again open and the coated compressed dosage form is ejected from the thermal cycle molding module.

Suitable thermoplastic materials for use in or as the flowable material include both water-soluble and water insoluble polymers that are generally linear, not crosslinked, and not strongly hydrogen bonded to adjacent polymer chains. Examples of suitable thermoplastic materials include: thermoplastic water-swellable cellulose derivatives, thermoplastic water insoluble cellulose derivatives, thermoplastic vinyl polymers, thermoplastic starches, thermoplastic polyalkylene glycols, thermoplastic polyalkylene oxides, and amorphous sugar-glass, and the like, and derivatives, copolymers, and combinations thereof. Examples of suitable thermoplastic water swellable cellulose derivatives include hydroxypropyl cellulose (HPC), hydroxypropylmethyl cellulose (HPMC), methyl cellulose (MC). Examples of suitable thermoplastic water insoluble cellulose derivatives include cellulose acetate (CA), ethyl cellulose (EC), cellulose acetate butyrate (CAB), cellulose propionate. Examples of suitable thermoplastic vinyl polymers include polyvinyl alcohol (PVA) and polyvinyl pyrrolidone (PVP). Examples of suitable thermoplastic starches are disclosed for example in U.S. Pat. No. 5,427,614. Examples of suitable thermoplastic polyalkylene glycols include polyethylene glycol. Examples of suitable thermoplastic polyalkylene oxides include polyethylene oxide having a molecular weight from about 100,000 to about 900,000 Daltons. Other suitable thermoplastic materials include sugar in the form on an amorphous glass such as that used to make hard candy forms.

Any film former known in the art is suitable for use in the flowable material. Examples of suitable film formers include, but are not limited to, film-forming water-soluble polymers, film-forming proteins, film-forming water insoluble polymers, and film-forming pH-dependent polymers. In one embodiment, the film-former for making the core or shell or portion thereof by molding may be selected from cellulose acetate, ammonium methacrylate copolymer type B, shellac, hydroxypropylmethylcellulose, and polyethylene oxide, and combinations thereof.

Suitable film-forming water soluble polymers include water soluble vinyl polymers such as polyvinyl alcohol (PVA); water soluble polycarbohydrates such as hydroxypropyl starch, hydroxyethyl starch, pullulan, methylethyl starch, carboxymethyl starch, pre-gelatinized starches, and film-forming modified starches; water swellable cellulose derivatives such as hydroxypropyl cellulose (HPC), hydroxypropylmethyl cellulose (HPMC), methyl cellulose (MC), hydroxyethylmethylcellulose (HEMC), hydroxybutylmethylcellulose (HBMC), hydroxyethylethylcellulose (HEEC), and hydroxyethylhydroxypropylmethyl cellulose (HEMPMC); water soluble copolymers such as methacrylic acid and methacrylate ester copolymers, polyvinyl alcohol and polyethylene glycol copolymers, polyethylene oxide and polyvinylpyrrolidone copolymers; and derivatives and combinations thereof.

Suitable film-forming proteins may be natural or chemically modified, and include gelatin, whey protein, myofibrillar proteins, coagulatable proteins such as albumin, casein, caseinates and casein isolates, soy protein and soy protein isolates, zein; and polymers, derivatives and mixtures thereof.

Suitable film-forming water insoluble polymers, include for example ethylcellulose, polyvinyl alcohols, polyvinyl acetate, polycaprolactones, cellulose acetate and its derivatives, acrylates, methacrylates, acrylic acid copolymers; and the like and derivatives, copolymers, and combinations thereof.

Suitable film-forming pH-dependent polymers include enteric cellulose derivatives, such as for example hydroxypropyl methylcellulose phthalate, hydroxypropyl methylcellulose acetate succinate, cellulose acetate phthalate; natural resins, such as shellac and zein; enteric acetate derivatives such as for example polyvinylacetate phthalate, cellulose acetate phthalate, acetaldehyde dimethylcellulose acetate; and enteric acrylate derivatives such as for example polymethacrylate-based polymers such as poly(methacrylic acid, methyl methacrylate) 1:2, which is commercially available from Rohm Pharma GmbH under the tradename, EUDRAGIT S, and poly(methacrylic acid, methyl methacrylate) 1:1, which is commercially available from Rohm Pharma GmbH under the tradename, EUDRAGIT L, and the like, and derivatives, salts, copolymers, and combinations thereof.

One suitable hydroxypropylmethylcellulose compound for use as a thermoplastic film-forming water soluble polymer is "HPMC 2910", which is a cellulose ether having a degree of substitution of about 1.9 and a hydroxypropyl molar substitution of 0.23, and containing, based upon the total weight of the compound, from about 29% to about 30% methoxyl groups and from about 7% to about 12% hydroxylpropyl groups. HPMC 2910 is commercially available from the Dow Chemical Company under the tradename METHOCEL E. METHOCEL E5, which is one grade of HPMC-2910 suitable for use in the present invention, has a viscosity of about 4 to 6 cps (4 to 6 millipascal-seconds) at 20° C. in a 2% aqueous solution as determined by a Ubbelohde viscometer. Similarly, METHOCEL E6, which is another grade of HPMC-2910 suitable for use in the present invention, has a viscosity of about 5 to 7 cps (5 to 7 millipascal-seconds) at 20° C. in a 2% aqueous solution as determined by a Ubbelohde viscometer. METHOCEL E15, which is another grade of HPMC-2910 suitable for use in the present invention, has a viscosity of about 15000 cps (15 millipascal-seconds) at 20° C. in a 2% aqueous solution as determined by a Ubbelohde viscometer. As used herein, "degree of substitution" means the average number of substituent groups attached to an anhydroglucose ring, and "hydroxypropyl molar substitution" means the number of moles of hydroxypropyl per mole anhydroglucose.

One suitable polyvinyl alcohol and polyethylene glycol copolymer is commercially available from BASF Corporation under the tradename KOLLICOAT IR.

As used herein, "modified starches" include starches that have been modified by crosslinking, chemically modified for improved stability or optimized performance, or physically modified for improved solubility properties or optimized performance. Examples of chemically modified starches are well known in the art and typically include those starches that have been chemically treated to cause replacement of some of its hydroxyl groups with either ester or ether groups. Crosslinking, as used herein, may occur in modified starches when two hydroxyl groups on neighboring starch molecules are chemically linked. As used herein, "pre-gelatinized starches" or "instantized starches" refers to modified starches that have been pre-wetted, then dried to enhance their cold-water solubility. Suitable modified starches are commercially available from several suppliers such as, for example, A.E. Staley Manufacturing Company, and National Starch & Chemical Company. One suitable film forming modified starch includes the pre-gelatinized waxy maize derivative starches that are commercially available from National Starch & Chemical Company under the tradenames PURITY GUM and FILM-SET, and derivatives, copolymers, and mixtures thereof. Such waxy maize starches typically contain, based upon the total weight of the starch, from about 0 percent to about 18 percent of amylose and from about 100% to about 88% of amylopectin.

Other suitable film forming modified starches include the hydroxypropylated starches, in which some of the hydroxyl groups of the starch have been etherified with hydroxypropyl groups, usually via treatment with propylene oxide. One example of a suitable hydroxypropyl starch that possesses film-forming properties is available from Grain Processing Company under the tradename, PURE-COTE B790.

Suitable tapioca dextrins for use as film formers include those available from National Starch & Chemical Company under the tradenames CRYSTAL GUM or K-4484, and derivatives thereof such as modified food starch derived from tapioca, which is available from National Starch and Chemical under the tradename PURITY GUM 40, and copolymers and mixtures thereof.

Any thickener known in the art is suitable for use in the flowable material of the present invention. Examples of such thickeners include but are not limited to hydrocolloids (also referred to herein as gelling polymers), clays, gelling starches, and crystallizable carbohydrates, and derivatives, copolymers and mixtures thereof.

Examples of suitable hydrocolloids (also referred to herein as gelling polymers) such as alginates, agar, guar gum, locust bean, carrageenan, tara, gum arabic, tragacanth, pectin, xanthan, gellan, maltodextrin, galactomannan, pusstulan, laminarin, scleroglucan, gum arabic, inulin, pectin, whelan, rhamsan, zooglan, methylan, chitin, cyclodextrin, chitosan. Examples of suitable clays include smectites such as bentonite, kaolin, and laponite; magnesium trisilicate, magnesium aluminum silicate, and the like, and derivatives and mixtures thereof. Examples of suitable gelling starches include acid hydrolyzed starches, and derivatives and mixtures thereof. Additional suitable thickening hydrocolloids include low-moisture polymer solutions such as mixtures of gelatin and other hydrocolloids at water contents up to about 30%, such as for example those used to make "gummy" confection forms.

Additional suitable thickeners include crystallizable carbohydrates, and the like, and derivatives and combinations thereof. Suitable crystallizable carbohydrates include the monosaccharides and the oligosaccharides. Of the monosaccharides, the aldohexoses e.g., the D and L isomers of allose, altrose, glucose, mannose, gulose, idose, galactose, talose, and the ketohexoses e.g., the D and L isomers of fructose and sorbose along with their hydrogenated analogs: e.g., glucitol (sorbitol), and mannitol are preferred. Of the oligosaccharides, the 1,2-disaccharides sucrose and trehalose, the 1,4-disaccharides maltose, lactose, and cellobiose, and the 1,6-disaccharides gentiobiose and melibiose, as well as the trisaccharide raffinose are preferred along with the isomerized form of sucrose known as isomaltulose and its hydrogenated analog isomalt. Other hydrogenated forms of reducing disaccharides (such as maltose and lactose), for example, maltitol and lactitol are also preferred. Additionally, the hydrogenated forms of the aldopentoses: e.g., D and L ribose, arabinose, xylose, and lyxose and the hydrogenated forms of the aldotetroses: e.g., D and L erythrose and throse are preferred and are exemplified by xylitol and erythritol, respectively.

In one embodiment of the invention, the flowable material comprises gelatin as a gelling polymer. Gelatin is a natural, thermogelling polymer. It is a tasteless and colorless mixture of derived proteins of the albuminous class that is ordinarily soluble in warm water. Two types of gelatin—Type A and Type B—are commonly used. Type A gelatin is a derivative of acid-treated raw materials. Type B gelatin is a derivative of alkali-treated raw materials. The moisture content of gelatin, as well as its Bloom strength, composition and original gelatin processing conditions, determine its transition temperature between liquid and solid. Bloom is a standard measure of the strength of a gelatin gel, and is roughly correlated with molecular weight. Bloom is defined as the weight in grams required to move a half-inch diameter plastic plunger 4 mm into a 6.67% gelatin gel that has been held at 10° C. for 17 hours. In a preferred embodiment, the flowable material is an aqueous solution comprising 20% 275 Bloom pork skin gelatin, 20% 250 Bloom Bone Gelatin, and approximately 60% water.

Suitable xanthan gums include those available from C. P. Kelco Company under the tradenames KELTROL 1000, XANTROL 180, or K9B310.

Suitable clays include smectites such as bentonite, kaolin, and laponite; magnesium trisilicate, magnesium aluminum silicate, and the like, and derivatives and mixtures thereof.

"Acid-hydrolyzed starch," as used herein, is one type of modified starch that results from treating a starch suspension with dilute acid at a temperature below the gelatinization point of the starch. During the acid hydrolysis, the granular form of the starch is maintained in the starch suspension, and the hydrolysis reaction is ended by neutralization, filtration and drying once the desired degree of hydrolysis is reached. As a result, the average molecular size of the starch polymers is reduced. Acid-hydrolyzed starches (also known as "thin boiling starches") tend to have a much lower hot viscosity than the same native starch as well as a strong tendency to gel when cooled.

"Gelling starches," as used herein, include those starches that, when combined with water and heated to a temperature sufficient to form a solution, thereafter form a gel upon cooling to a temperature below the gelation point of the starch. Examples of gelling starches include, but are not limited to, acid hydrolyzed starches such as that available from Grain Processing Corporation under the tradename PURE-SET B950; hydroxypropyl distarch phosphate such as that available from Grain Processing Corporation under the tradename, PURE-GEL B990, and mixtures thereof.

Suitable low-melting hydrophobic materials include fats, fatty acid esters, phospholipids, and waxes. Examples of suitable fats include hydrogenated vegetable oils such as for example cocoa butter, hydrogenated palm kernel oil, hydrogenated cottonseed oil, hydrogenated sunflower oil, and hydrogenated soybean oil; and free fatty acids and their salts. Examples of suitable fatty acid esters include sucrose fatty acid esters, mono-, di-, and tri-glycerides, glyceryl behenate, glyceryl palmitostearate, glyceryl monostearate, glyceryl tristearate, glyceryl trilaurylate, glyceryl myristate, Glyco-Wax-932, lauroyl macrogol-32 glycerides, and stearoyl macrogol-32 glycerides. Examples of suitable phospholipids include phosphotidyl choline, phosphotidyl serene, phosphotidyl enositol, and phosphotidic acid. Examples of suitable waxes include carnauba wax, spermaceti wax, beeswax, candelilla wax, shellac wax, microcrystalline wax, and paraffin wax; fat-containing mixtures such as chocolate; and the like.

Suitable non-crystallizable carbohydrates include non-crystallizable sugars such as polydextrose, and starch hydrolysates, e.g. glucose syrup, corn syrup, and high fructose corn syrup; and non-crystallizable sugar-alcohols such as maltitol syrup.

Suitable solvents for optional use as components of the flowable material for making the core or the shell by molding include water; polar organic solvents such as methanol, ethanol, isopropanol, acetone, and the like; and non-polar organic solvents such as methylene chloride, and the like; and mixtures thereof.

The flowable material for making cores or the shell by molding may optionally comprise adjuvants or excipients, which may comprise up to about 30% by weight of the flowable material. Examples of suitable adjuvants or excipients include plasticizers, detackifiers, humectants, surfactants, anti-foaming agents, colorants, flavorants, sweeteners, opacifiers, and the like. Suitable plasticizers for making the core, the shell, or a portion thereof, by molding include, but not be limited to polyethylene glycol; propylene glycol; glycerin; sorbitol; triethyl citrate; tributyl citrate; dibutyl sebecate; vegetable oils such as castor oil, rape oil, olive oil, and sesame oil; surfactants such as Polysorbates, sodium lauryl sulfates, and dioctyl-sodium sulfosuccinates; mono acetate of glycerol; diacetate of glycerol; triacetate of glycerol; natural gums; triacetin; acetyltributyl citrate; diethyloxalate; diethylmalate; diethyl fumarate; diethylmalonate; dioctylphthalate; dibutylsuccinate; glyceroltributyrate; hydrogenated castor oil; fatty acids; substituted triglycerides and glycerides; and the like and/or mixtures thereof. In one embodiment, the plasticizer is triethyl citrate. In certain embodiments, the shell is substantially free of plasticizers, i.e. contains less than about 1%, say less than about 0.01% of plasticizers.

In embodiments in which the shell is prepared using a solvent-free molding process, the shell typically comprises at least about 30 percent, e.g. at least about 45 percent by weight of a thermal-reversible carrier. The shell may optionally further comprise up to about 55 weight percent of a release-modifying excipient. The shell may optionally further comprise up to about 30 weight percent total of various plasticizers, adjuvants and excipients. In certain embodiments in which the shell is prepared by solvent-free molding, and functions to delay the release of one or more active ingredients from an underlying core, the release modifying excipient is preferably selected from swellable, erodible hydrophilic materials.

In embodiments in which the shell is prepared using a solvent-based molding process, the shell typically comprises at least about 10 weight percent, e.g. at least about 12 weight percent or at least about 15 weight percent or at least about 20 weight percent or at least about 25 weight percent of a film-former. Here, the shell may optionally further comprise up to about 55 weight percent of a release-modifying excipient. The shell may again also optionally further comprise up to about 30 weight percent total of various plasticizers, adjuvants, and excipients.

In embodiments in which the shell is applied to the cores by molding, at least a portion of the shell surrounds the cores such that the shell inner surface resides substantially conformally upon the outer surfaces of the cores. As used herein, the term "substantially conformally" means that the inner surface of the shell has peaks and valleys or indentations and protrusions corresponding substantially inversely to the peaks and valleys of the outer surface of the core. In certain such embodiments, the indentations and protrusions typically have a length, width, height or depth in one dimension of greater than 10 microns, say greater than 20 microns, and less than about 30,000 microns, preferably less than about 2000 microns.

The total weight of the shell is preferably about 20 percent to about 400 percent of the total weight of the cores. In embodiments wherein the shell is prepared by a solvent-free molding process, the total weight of the shell is typically from about 50 percent to about 400 percent, e.g. from about 75 percent to about 400 percent, or about 100 percent to about 200 percent of the total weight of the cores. In embodiments wherein the shell is prepared by a solvent-based molding process, the total weight of the shell is typically from about 20 percent to about 100 percent of the total weight of the cores.

The thickness of the shell is important to the release properties of the dosage form. Advantageously, the dosage forms of the invention can be made with precise control over shell thickness, in particular using the zero cycle, thermal cycle or thermal setting injection molding methods and apparatus described above. Typical shell thicknesses that may be employed are about 50 to about 4000 microns. In certain preferred embodiments, the shell has a thickness of less than 800 microns. In embodiments wherein the shell portion is prepared by a solvent-free molding process, the shell portion typically has a thickness of about 500 to about 4000 microns, e.g. about 500 to about 2000 microns, say about 500 to about 800 microns, or about 800 to about 1200 microns. In embodiments wherein the shell portion is prepared by a solvent-based molding process, the shell portion typically has a thickness of less than about 800 microns, e.g. about 100 to about 600 microns, say about 150 to about 400 microns. In a particularly preferred embodiment the dosage form comprises first and second cores and first and second shell portions, and at least one of the shell portions has a thickness of less than about 800 microns, e.g. about 100 to about 600 microns, e.g. about 150 to about 400 microns.

In certain embodiments, the shell is formed by injection molding in a shape having recesses to permit the subsequent incorporation or addition of one or more cores or plurality of coated particles into corresponding recesses. Additional shell material can optionally be provided over the one or more cores or plurality of particles, followed by the provision of fill material over at least a portion of the one or more cores. In embodiments in which the shell and/or fill material is prepared by molding, the fill material and/or shell are substantially devoid of pores. Preferably, the fill or shell materials are typically substantially free of pores in the diameter range of 0.5 to 5.0 microns, i.e. has a pore volume in the pore diameter range of 0.5 to 5.0 microns of less than about 0.02 cc/g, preferably less than about 0.01 cc/g, more preferably less than about 0.005 cc/g. Typical compressed materials have pore volumes in this diameter range of more than about 0.02 cc/g.

Pore volume, pore diameter and density may be determined using a Quantachrome Instruments PoreMaster 60 mercury intrusion porosimeter and associated computer software program known as "Porowin." The procedure is documented in the Quantachrome Instruments PoreMaster Operation Manual. The PoreMaster determines both pore volume and pore diameter of a solid or powder by forced intrusion of a non-wetting liquid (mercury), which involves evacuation of the sample in a sample cell (penetrometer), filling the cell with mercury to surround the sample with mercury, applying pressure to the sample cell by: (i) compressed air (up to 50 psi maximum); and (ii) a hydraulic (oil) pressure generator (up to 60000 psi maximum). Intruded volume is measured by a change in the capacitance as mercury moves from outside the sample into its pores under applied pressure. The corresponding pore size diameter (d) at which the intrusion takes place is calculated directly from the so-called "Washburn Equation": $d=-(4\gamma(\cos\theta)/P)$ where $\gamma$ is the surface tension of liquid mercury, $\theta$ is the contact angle between mercury and the sample surface and P is the applied pressure.

In those embodiments in which solvent-free molding is employed, the flowable material may comprise a thermal-reversible carrier. Suitable thermal-reversible carriers for use in making a core, the shell or both by molding are thermoplastic materials typically having a melting point below about 110° C., more preferably between about 20 and about 100° C. Examples of suitable thermal-reversible carriers for solvent-free molding include thermoplastic polyalkylene glycols, thermoplastic polyalkylene oxides, low melting hydrophobic materials, thermoplastic polymers, thermoplastic starches, and the like. Preferred thermal-reversible carriers include polyethylene glycol and polyethylene oxide. Suitable thermoplastic polyalkylene glycols for use as thermal-reversible carriers include polyethylene glycol having molecular weight from about 100 to about 20,000, e.g. from about 100 to about 8,000 Daltons.

Suitable thermoplastic polyalkylene oxides include polyethylene oxide having a molecular weight from about 100,000 to about 900,000 Daltons. Suitable low-melting hydrophobic materials for use as thermal-reversible carriers include fats, fatty acid esters, phospholipids, and waxes which are solid at room temperature, fat-containing mixtures such as chocolate; and the like. Examples of suitable fats include hydrogenated vegetable oils such as for example cocoa butter, hydrogenated palm kernel oil, hydrogenated cottonseed oil, hydrogenated sunflower oil, and hydrogenated soybean oil; and free fatty acids and their salts. Examples of suitable fatty acid esters include sucrose fatty acid esters, mono, di, and triglycerides, glyceryl behenate, glyceryl palmitostearate, glyceryl monostearate, glyceryl tristearate, glyceryl trilaurylate, glyceryl myristate, GlycoWax-932, lauroyl macrogol-32 glycerides, and stearoyl macrogol-32 glycerides. Examples of suitable phospholipids include phosphotidyl choline, phosphotidyl serene, phosphotidyl enositol, and phosphotidic acid. Examples of suitable waxes that are solid at room temperature include carnauba wax, spermaceti wax, beeswax, candelilla wax, shellac wax, microcrystalline wax, and paraffin wax.

Suitable thermoplastic polymers for use as thermal-reversible carriers include thermoplastic water swellable cellulose derivatives, thermoplastic water insoluble polymers, thermoplastic vinyl polymers, thermoplastic starches, and thermoplastic resins, and combinations thereof. Suitable thermoplastic water swellable cellulose derivatives include hydroxypropylmethyl cellulose (HPMC), methyl cellulose (MC), carboxymethylcellulose (CMC), cross-linked hydroxypropylcellulose, hydroxypropyl cellulose (HPC), hydroxybutylcellulose (HBC), hydroxyethylcellulose (HEC), hydroxypropylethylcellulose, hydroxypropylbutylcellulose, hydroxypropylethylcellulose, and salts, derivatives, copolymers, and combinations thereof. Suitable thermoplastic water insoluble polymers include ethylcellulose, polyvinyl alcohols, polyvinyl acetate, polycaprolactones, cellulose acetate and its derivatives, acrylates, methacrylates, acrylic acid copolymers, and the like and derivatives, copolymers, and combinations thereof. Suitable thermoplastic vinyl polymers include polyvinylacetate, polyvinyl alcohol, and polyvinyl pyrrolidone (PVP). Examples of suitable thermoplastic starches for use as thermal-reversible carriers are disclosed for example in U.S. Pat. No. 5,427,614. Examples of suitable thermoplastic resins for use as thermal-reversible carriers include dammars, mastic, rosin, shellac, sandarac, and glycerol ester of rosin. In one embodiment, the thermal-reversible carrier for making a core by molding is selected from polyalkylene glycols, polyalkylene oxides, and combinations thereof.

In embodiments in which the shell comprises an active ingredient intended to have immediate release from the dosage form, the shell is preferably prepared via solvent-free molding. In such embodiments a thermal-reversible carrier is employed in the flowable material to make the shell, said thermal-reversible carrier preferably selected from polyethylene glycol with weight average molecular weight from about 1450 to about 20000, polyethylene oxide with weight average molecular weight from about 100,000 to about 900,000, and the like.

In certain embodiments, the shell or a shell portion functions as an eroding matrix from which active ingredient dispersed in the shell is liberated by the dissolution of successive layers of the shell surface. In these embodiments, the rate of active ingredient release will depend on the dissolution rate of the matrix material in the shell or shell portion. Particularly useful matrix materials for providing surface erosion include those that first absorb liquid, then swell and/or gel prior to dissolving. In certain such embodiments, the shell or shell portion preferably comprises a release modifying moldable excipient comprising a swellable erodible hydrophilic material.

In certain other embodiments, the shell or a portion thereof functions as a barrier to prevent release therethrough of an active ingredient contained in an underlying core. In such embodiments, active ingredient is typically released from a portion of the core that is not covered by that portion of the shell, for example from a portion of the core in communication with one or more openings in the shell. Such embodiments advantageously allow for control of the surface area for release of the active ingredient. In certain embodiments for example, the surface area for release of active ingredient can be maintained substantially constant over time. In a particularly preferred embodiment, the release of at least one active ingredient follows substantially zero-order kinetics. In such embodiments, the shell preferably comprises a modified release composition comprising a water insoluble material, for example a water insoluble polymer.

In other embodiments, the shell, or a shell portion functions as a delayed release coating to delay release of one or more active ingredients contained in an underlying core. In these embodiments, the lag-time for onset of active ingredient release may be governed by erosion of the shell, diffusion of active ingredient through the shell, or a combination thereof. In certain such embodiments, the shell preferably comprises a release modifying moldable excipient comprising a swellable erodible hydrophilic material.

The following non-limiting example further illustrates the claimed invention.

Example 1

A dosage form according to the invention providing a double pulse release of ibuprofen is manufactured by a molding process as follows. The double pulse consists of a 200 mg immediate release (IR) ibuprofen followed by a 100 mg burst release of ibuprofen after a predetermined lag time.

Part A. Preparation of the 200 mg Immediate-Release (IR) Ibuprofen Core

Formulation:

| Ingredients | Trade Name | Manufacturer | Mg/Tablet |
|---|---|---|---|
| Ibuprofen granules (115 microns) | | Albemarle Corp. Orangeburg, SC | 200.0 |
| Sodium starch glycolate | Explotab ® | Penwest Pharmaceuticals Co. Patterson, NJ | 12.0 |
| Colloidal silicon dioxide | Cab-O-Sil LM-5 ® | Cabot Corp. Tuscola, IL | 1.0 |
| Total | | | 213.0 |

Manufacturing Process:

Ibuprofen and sodium starch glycolate are delumped through a 30 mesh screen and said ingredients are mixed in a 2 qt. twin-shell blender for 5 minutes. Colloidal silicon dioxide is also delumped through a 30 mesh screen and is added to the aforementioned mixture for blending for another 5 minutes. Prescreened (through a 30 mesh screen) ibuprofen and sodium starch glycolate are mixed in a 2 qt. twin shell blender for 5 minutes.

A rotary tablet press equipped with round punch and die unit with a diameter of 0.250" is used to make the first core as a tablet. The final blend (from Step 1) is fed into the die of the tablet press and is compressed into a tablet core under 2000 lb/in² of operating pressure. The weight of compressed tablet is 213.0 mg, which contains 200.0 mg of ibuprofen.

Part B. Preparation of the 100 mg Immediate-Release (IR) Ibuprofen Core

Formulation:

| Ingredient | Trade Name | Manufacturer | Mg/Tablet |
|---|---|---|---|
| Ibuprofen (115 microns) | | Albemarle Corp. Orangeburg, SC | 100.0 |
| Microcrystalline cellulose | Avicel pH 101 ® | FMC Corp. Newark, DE 19711 | 106.5 |
| Sodium starch glycolate | Explotab ® | Penwest Pharmaceuticals Co. Patterson, NJ | 6.0 |
| Colloidal silicon dioxide | Cab-O-Sil LM-5 ® | Cabot Corp. Tuscola, IL | 0.5 |
| Total | | | 213.0 |

Manufacturing Process:

Ibuprofen, microcrystalline cellulose and sodium starch glycolate are delumped through a 30 mesh screen and said ingredients are mixed in a 2 qt. twin shell blender for 5 minutes. Colloidal silicon dioxide is also delumped through a 30 mesh screen and is added to the aforementioned mixture for blending for another 5 minutes.

A rotary tablet press equipped with round punch and die unit with a diameter of 0.250" is used to make the second core as a tablet. The final blend (from Step 1) is fed into the die and is compressed into a tablet core under 2000 lb/in² of operating pressure. The weight of compressed tablet is 213.0 mg, which contains 100.0 mg of ibuprofen.

Part C. Preparation and Application of the Shell by Solvent-Based Molding:

A polymeric composition suitable for use as a shell for a dosage form and having the formula set forth in Table A below was prepared as follows:

TABLE A

Shell Portion: Formulation of Polymeric Composition

| Ingredient | Trade Name | Manufacturer | Weight %* |
|---|---|---|---|
| Water | — | — | 17.17 |
| Acetone | B&J Brand R High Purity Solvent | Honeywell International Inc., Muskegon, MI | 40.08 |
| Cellulose Acetate | Cellulose Acetate, NF | Eastman Chemical Company, Kingsport, TN | 22.90 |
| Carrageenan | Gelcarin GP-812, NF | FMC Corporation, Pharmaceutical Division, Newark, DE | 0.76 |
| Triacetin | Triacetin, Food Grade | Eastman Chemical Company, Kingsport, TN | 15.27 |
| Polyethylene Glycol 400 | Polyethylene Glycol 400 NF, FCC Grade | The Dow Chemical Company, Midland, MI | 3.82 |

*weight percentage of active ingredient based upon total wet weight of the polymeric composition The cellulose acetate is added to a beaker containing acetone, triacetin, polyethylene glycol, and water and mixed using a mixer until all powder is dissolved. The mixture is then heated in the 55° C. water bath to obtain a viscous solution. The carrageenan is then added to the hot solution, and the resulting mixture is heated and stirred until a homogeneous texture is obtained.

Part D: Preparation of First Fill Material: for Immediate Release

The first fill material is prepared for application to the first core portion prepared in Part A. The first fill material comprises red gelatin for immediate release, and is made of the following ingredients: purified water, Opatint Red DD-1761, and 275 Bloom Pork Skin Gelatin added together as a mix of dry gelatin granules. A gelatin slurry is formed from these ingredients and heated to 55° C. to melt and dissolve the gelatin. The gelatin solution is held at 55° C. for approximately 3 hours (holding times at this temperature can generally range between about 2 and about 16 hours). The solution is then mixed until uniform (about 5 to 15 minutes). The gelatin solution is maintained at 55° C. with continuous mixing during its use in the first thermal cycling molding module.

Part E. Preparation of Second Fill Material for Delayed Burst Release

The second fill material is prepared for application to the second core portion in Part B. The second fill material is prepared using a dispersion containing 80 parts of hydroxypropyl methylcellulose (HPMC) having a viscosity of about 4000 mPa s in 2% aqueous solution [commercially available from Dow Chemical as METHOCEL K4M]; and 20 parts of Kappa Carrageenan in 471 parts of purified water. The solution has a solids concentration of 17.5%. First, carrageenan is dispersed in room temperature water with an electric mixer equipped with a propeller style blade to form a liquid carrier. Next, the carrageenan/water dispersion is heated to about 80° C. with continued mixing. Next, the HPMC is dispersed in the liquid carrier with the propeller mixer, and mixing continued to maintain the HPMC in a suspended state.

Laboratory Manufacturing Process for Application of the Shell and Fill Materials A laboratory scale thermal cycle molding unit having an overall caplet shape of dimensions of 0.700"×0.350"×0.06", is used to apply the shell portion to the cores. The molding unit comprises a single mold assembly made from an upper mold assembly portion comprising an upper mold cavity, and a lower mold assembly portion comprising a lower mold cavity. The lower mold assembly portion is first cooled to 5° C. The shell material of Part C is introduced into the lower mold cavity. Two separate cores prepared, as described in aforementioned Parts A and B, are immediately inserted into two stations within the cavity. The in-process dosage form is held in the chilled mold for 20 seconds to allow the shell material to harden. The stations separate the two cores within the lower mold cavity by 1 mm.

A blank upper mold assembly portion is mated with the lower mold assembly portion. The upper mold cavity comprises a small rod (0.1 mm in diameter×1 mm in length) attached to its inner surface that contacts one station for one of the cores to allow a portion of the dosage form to remain uncoated. The shell material of Part C is introduced into the upper mold cavity. The lower mold assembly portion, which has been maintained at 5° C., is mated with the upper mold assembly portion in such a way that the cores of Part A (200 mg ibuprofen tablet) and Part B (100 mg of ibuprofen tablet) is mated with the first core station of the upper mold assembly. The shell material of Part C is introduced into the lower mold cavity and held at 5° C. for 30 seconds to harden.

The first fill material portion is injected into the upper mold portion and covers the portion of the first core that was not previously covered by the shell. The second fill material portion is simultaneously injected into the upper mold portion and covers the portion of the second core that was not previously covered by the shell. The upper mold is held at 5° C. for 60 seconds to allow the first and second fill material portions to harden. The lower mold assembly portion is then removed and the finished dosage form, a molded caplet coated with a shell material and two fill materials, is ejected from the upper mold cavity. The weight gain from the shell material (i.e. the difference in weight between the finished dosage form and the core) is recorded.

Manufacturing Process for Application of the Shell and Fill Materials:

Dosage forms of the invention are made in a continuous process using an apparatus comprising two thermal cycle molding modules linked in series via a transfer device as described at pages 14-16 of copending U.S. application Ser. No. 09/966,939, the disclosure of which is incorporated herein by reference. The dosage forms comprise two cores coated with a shell and a first and second fill portion.

The thermal cycle molding modules have the general configuration shown in FIG. 3 and pages 27-51 of copending U.S. application Ser. No. 09/966,497, which depicts a thermal cycle molding module 200 comprising a rotor 202 around which a plurality of mold units 204 are disposed. The thermal cycle molding modules include reservoirs 206 (see FIG. 4) for holding the shell material, the first fill material, and the second fill material. In addition, each thermal cycle molding module is provided with a temperature control system for rapidly heating and cooling the mold units. FIGS. 55 and 56 of pending U.S. application Ser. No. 09/966,497 depict the temperature control system 600.

The transfer device has the structure shown as 300 in FIG. 3 and described on pages 51-57 of copending U.S. application Ser. No. 09/966,414, the disclosure of which is incorporated by reference. It comprises a plurality of transfer units 304 attached in cantilever fashion to a belt 312 as shown in FIGS. 68 and 69. The transfer device rotates and operates in sync with the thermal cycle molding modules to which it is coupled. Transfer units 304 comprise retainers 330 for holding the cores as they travel around the transfer device.

The transfer device transfers the cores aforementioned in Part A and Part B to the second molding module, which applies the shell to the cores. The second thermal cycle molding module is of the type shown in FIG. 28A of copending U.S. application Ser. No. 09/966,497. The mold units 204 of the second thermal cycle molding module comprise upper mold assemblies 214, rotatable center mold assemblies 212 and lower mold assemblies 210 as shown in FIG. 28C. Cores are continuously transferred to the mold assemblies, which then close over the cores.

At the beginning of the molding cycle (rotor at the 0 degree position) the mold assemblies are in the open position. Center mold assembly 212 as shown in copending U.S. application Ser. No. 09/966,497 as incorporated herein by reference, has received the compressed cores, for example from a compression module according to the invention transferred via a transfer device also according to the invention. As the rotor continues to revolve, the upper mold assembly 214 closes against center mold assembly 212. Next, flowable material is injected into the mold cavity created by union of the mold assemblies to apply a shell from Part C to the first half of the dosage form. The flowable material is cooled in the mold cavity. The mold assemblies open with the partially coated dosage forms remaining in the upper mold assembly 214. Upon further revolution of the rotor, the center mold assembly rotates 180 degrees. As the rotor moves past 180 degrees the mold assemblies again close and the uncoated portion of the compressed dosage form is covered with flowable material thus forming a shell having an opening aligned with the fill material, in a mold assembly that contains one or more protrusions, which prevent a portion of the cores from being covered. The protrusions also contain nozzles for injecting the fill materials. The protrusions retract following the application of the second portion of the shell from Part C, and the flowable fill material from Part D and the fill material from Part E, heated to a flowable state in reservoirs 206, are injected into the uncoated portions of the dosage form, over a portion of the cores from Part A and Part B, forming the fill portions 16 as shown in FIG. 1. A molding cycle is completed with setting or hardening of the shell and fill materials on the second half of the compressed dosage form. The mold assemblies again open and the coated compressed dosage form is ejected from the molding module.

Although this invention has been illustrated by reference to specific embodiments, it will be apparent to those skilled in the art that various changes and modifications may be made which clearly fall within the scope of this invention.

We claim:

1. A medicinal dosage form comprising:
   a first core and a second core,
   wherein said first core comprises a first active ingredient and said second core comprises a second active ingredient,
   wherein said first core and said second core each have a diameter of at least about 6.35 millimeters, respectively, and
   a shell that is provided over and having a surface conforming or defining a first portion of said first core and a first portion of said second core,
   a first fill material provided over and having a surface conforming to or defining a second portion of said first core,
   wherein the first fill material does not overlap with the shell along the circumference of the core, wherein said fill material covers said second portion of said first core and said second portion of said second core exclusively and does not cover said first portion of said first core or said first portion of said second core,
   wherein the first active ingredient is released through the first fill material, and wherein the first active ingredient is not released through the shell, and
   a second fill material provided over and having a surface conforming to or defining a second portion of said second core,
   wherein the second fill material does not overlap with the shell along the circumference of the core,
   wherein the second active ingredient is released through the second fill material, and
   wherein the second active ingredient is not released through the shell;
   wherein the first fill material in contact with said first core is not in contact with any portion of said second core,
   wherein the second fill material in contact with said second core is not in contact with any portion of said first core,
   wherein the first fill material provides for immediate release of the first active ingredient,
   wherein the second fill material provides for delayed, sustained, prolonged, extended, pH-dependent, or retarded release of the second active ingredient,
   wherein said first core and said second core are each selected from the group consisting of a tablet, a capsule, a suppository, a confectionery, a semi-solid in finished dosage form and a liquid in finished dosage form.

2. A dosage form according to claim 1, wherein the first fill material and the second fill material are each substantially devoid of pores having a diameter of 0.5 to 5.0 microns.

3. A dosage form according to claim 1, wherein the first fill material, the second fill material and the shell are substantially devoid of pores having a diameter of 0.5 to 5.0 microns.

4. A dosage form according to claim 1, wherein the first fill material, the second fill material or both the first fill material and the second fill material extends above the surface level of the shell.

5. A dosage form according to claim 1, wherein the dosage form further comprises a third core that has a first portion having a shell material that has been provided over and with a surface conforming thereto or defining a recess therein and a second portion that has been provided with a fill material with a surface conforming thereto.

6. A dosage form according to claim 1, wherein the shell is substantially free of pores having a diameter of 0.5 to 5.0 microns.

7. A dosage form according to claim 1, wherein the shell provides for delayed, sustained, prolonged, extended, or retarded release of at least one active ingredient contained in the second core.

8. A dosage form according to claim 1, wherein the shell comprises at least one material that is insoluble, semi-permeable, pH-dependent, or erodible in an aqueous environment.

9. A dosage form according to claim 1, wherein the second fill material comprises material that is insoluble, semi-permeable, pH-dependent, or erodible in a liquid medium to provide said delayed release of active.

10. A dosage form according to claim 1, wherein a plurality of beads containing a pharmaceutically active ingredient are formed as a core within a defined recess of the shell.

* * * * *